(12) United States Patent
Lanza et al.

(10) Patent No.: US 6,287,558 B1
(45) Date of Patent: Sep. 11, 2001

(54) DEVICES CONTAINING CELLS OR TISSUE AND AN AGENT THAT INHIBITS DAMAGE BY A HOST CELL MOLECULE

(75) Inventors: Robert P. Lanza, Clinton; Dawn M. Ecker, Shrewsbury; John Ringeling, Boston; Joanne P. Marsh, Shrewsbury; William Chick, Wellesley, all of MA (US)

(73) Assignee: BioHybrio Technologies LLC, Shrewsbury, MA (US)

( * ) Notice: Subject to any disclaimer, the term of this patent is extended or adjusted under 35 U.S.C. 154(b) by 0 days.

(21) Appl. No.: 08/904,808

(22) Filed: Aug. 1, 1997

(51) Int. Cl.[7] .......................... A61K 35/12; C12N 11/00; C12N 11/04; C12N 5/00
(52) U.S. Cl. .................. 424/93.7; 424/130.1; 424/423; 435/177; 435/178; 435/182; 435/382; 435/395; 435/397; 436/528; 436/529; 436/535; 530/812; 530/813; 530/817
(58) Field of Search .................................. 435/174, 177, 435/178, 182, 395, 397, 382; 424/93.7, 423, 130.1; 436/528, 529, 535; 530/812, 813, 817

(56) References Cited

U.S. PATENT DOCUMENTS

| | | | |
|---|---|---|---|
| 4,353,888 | 10/1982 | Sefton | 424/25 |
| 4,391,909 | 7/1983 | Lim | 435/178 |
| 4,532,123 | 7/1985 | Gardner | 424/21 |
| 4,744,933 | 5/1988 | Rha et al. | 264/4.3 |
| 4,806,355 | 2/1989 | Goosen et al. | 424/424 |
| 4,933,185 | 6/1990 | Wheatley et al. | 424/461 |
| 5,011,472 * | 4/1991 | Aebischer et al. | 604/50 |
| 5,084,350 | 1/1992 | Chang et al. | 428/402.2 |
| 5,211,945 | 5/1993 | Wallach et al. | 424/85.1 |
| 5,227,298 | 7/1993 | Weber et al. | 435/178 |
| 5,330,768 | 7/1994 | Park et al. | 424/501 |
| 5,418,154 * | 5/1995 | Aebischer et al. | 435/182 |
| 5,459,054 | 10/1995 | Skjak-Braek et al. | 435/178 |
| 5,512,544 | 4/1996 | Wallach et al. | 514/12 |
| 5,543,158 | 8/1996 | Gref et al. | 424/501 |
| 5,578,325 | 11/1996 | Domb et al. | 424/501 |
| 5,626,862 | 5/1997 | Brem et al. | 424/426 |
| 5,651,980 | 7/1997 | Lanza et al. | 424/424 |
| 5,980,889 * | 11/1999 | Butler et al. | 424/93.7 |
| 6,083,523 * | 7/2000 | Dionne et al. | 424/424 |

FOREIGN PATENT DOCUMENTS

| | | |
|---|---|---|
| 2024196 | 12/1991 | (CA) . |
| 0 127 713 | 12/1984 | (EP) . |
| 0 127 989 | 12/1984 | (EP) . |
| 0 188 309 | 7/1986 | (EP) . |
| 0 301 777 | 2/1989 | (EP) . |
| 0 433 900 | 6/1991 | (EP) . |
| 0 512 528 | 11/1992 | (EP) . |
| 0 526 905 | 2/1993 | (EP) . |
| 0 606 869 | 7/1994 | (EP) . |
| 1236885 | 6/1971 | (GB) . |
| 1257178 | 12/1971 | (GB) . |
| 1983-357725 | 11/1983 | (JP) . |
| 2119734 | 11/1983 | (GB) . |
| WO 83/03061 | 9/1983 | (WO) . |
| WO 92/19195 | 11/1992 | (WO) . |
| WO 93/24112 | 12/1993 | (WO) . |
| WO 94/12161 | 6/1994 | (WO) . |
| WO 94/15589 | 7/1994 | (WO) . |
| WO 95/19743 | 7/1995 | (WO) . |
| WO 95/31206 | 11/1995 | (WO) . |

OTHER PUBLICATIONS

Abbas, A. et al.,"Effector mechanisms of Immune Responses", *Cell & Molecular Immunology*, 2nd Edition, Saunders Press Philadelpia, Ch. 12, pp. 240–260 (1994).

Cerra, F.,"Hypermetabolism, Organ Failure, and Metabolic Support", *Surgery*, vol. 101 (1), pp. 1–14 (1987).

Chang, T.,"Artificial Cells in Immobilization Biotechnology", *Biomat. Art Cells & Immob. Biotech.*, vol. 20 (5), pp. 1121–1143 (1992).

Chang, T.,"Artificial Cells: The Use of Hybrid Systems", *Artificial Organs*, vol. 4 (4), pp. 264–271 (1980).

Chang, T.,"Bioencapsulation in Biotechnology", *Biomat. Art Cells & Immob. Biotech.*, vol. 21 (3), pp. 291–297 (1993).

Chang, T.,"Blood Substitutes Based on Modified Hemoglobin Prepared by Encapsulation or Crosslinking: An Overview", *Biomat. Art. Cells & Immob. Biotech.*, vol. 20 (2–4), pp. 159–179 (1992).

Chang, T.,"Living Cells and Microorganisms Immobilized by Microencapsulation Inside Artificial Cells", *Fundamentals of Animal Cell Encapsulation and Immobilization* by Matthew F. Goosen (London: CRC Press), Chapter 8, pp. 183–196 (1993).

Chang, T.,"Semipermeable Aqueous Microcapsules", Ph.D. Thesis (McGill University, Department of Physiology, Montreal) 1965.

(List continued on next page.)

Primary Examiner—David M. Naff

(57) ABSTRACT

A device that includes a living cell or tissue and an agent that inhibits the ability of a host molecule to damage the cell or tissue. The device can be constructed in various forms including an implantable device, a composite microreactor and a double composite microreactor. The composite microreactor includes an internal particle that includes a living cell or tissue, an internal particle matrix that includes the living cell or tissue and an internal semipermeable coating enclosing the internal particle matrix, a gel super matrix in which the internal particle is embedded, and an agent that inhibits the ability of a host molecule to damage the cell or tissue. The double composite microreactor includes an internal particle, a particle that includes a particle matrix in which the internal particle is embedded, a super matrix in which the particle is embedded, and an agent that inhibits the ability of a host molecule to damage the living cell or tissue.

47 Claims, 2 Drawing Sheets

OTHER PUBLICATIONS

Chang, T.,"Semipermeable Aqueous Microcapsules", *Canadian Journal of Physiology and Pharmacology*, vol. 44, pp. 115–128 (1966).

Dahinden, C. et al.,"Regulation of Cytokine Expression by Human Blood Basophils", *Int. Arch. of Allergy and Immunology*, vol. 113, pp. 134–137 (1997).

de Oca, J. et al.,"21–Aminosteroid U–74389G (Lazaroid) Inhibits Bacterial Translocation after Small Bowel Transplantation in Rats", *Transplantation Proceedings*, vol. 29, pp. 1803 (1997).

Dupuy, B. et al.,"Microencapsulation of Isolated Pituitary Cells by Polyacrylamide Microlatex Coagulation on Agarose Beads", *Biomaterials*, vol. 12, pp. 493–496 (1991).

Essayan, D. et al.,"Regulation of Interleukin–13 by Type 4 Cyclic Nucleotide Phosphodiesterase (PDE) Inhibitors in Allergen–Specific Human T Lymphocyte Clones", *Biochemical Pharmacology*, vol. 53, pp. 1055–1060 (1997).

Fici, G. et al.,"Effects of Lazaroids and a Peroxynitrite Scavenger in a Cell Model of Peroxynitrite Toxicity", *Free Radical Biology & Medicine*, vol. 22 (1–2), pp. 223–228 (1997).

Goodman, A. et al.,"Long Pentraxins: an Emerging Group of Proteins with Diverse Functions", *Cytokine & Growth Factor Reviews*, vol. 7 (2), pp. 191–202 (1996).

Goosen, M.,"Insulin Delivery Systems and the Encapsulation of Cells for Medical and Industrial Use", *CRC Critical Reviews in Biocompatibility*, vol. 3 (1), pp. 1–24 (1987).

Goosen, M. et al.,"Immobilization of Living Cells in Biocompatible Semipermeable Microcapsules: Biomedical and Potential Biochemical Engineering Applications", *Polymers in Medicine II: Biomedical and Pharmaceutical Applications*, Chiellini et al. (eds), Plenum Press, NY, pp. 235–246 (1985).

Grasbon–Frodl, E. et al.,"Mesencephalic Neuron Death Induced by Congeners of Nitrogen Monoxide is Prevented by the Lazaroid U–83836E",*Exp. Brain Res.,*vol. 113, pp. 138–143 (1997).

Ishizaki, N. et al.,"Comparison of Various Lazaroid Compounds for Protection Against Ischemic Liver Injury", *Transplantation Proceedings*, vol. 29, pp. 1333–1334 (1997).

Ito, Y. et al.,"In vitro Study of Multicellular Hepatocyte Spheroids Formed in Microcapsules", *Artif. Organs*, vol. 16 (4), pp. 422–427 (1992).

Joyce, D. et al.,"Two Inhibitors of Pro–inflammatory Cytokine Release, Interleukin–10 and Interleukin–4, have Contrasting Effects on Release of Soluble p75 Tumor Necrosis Factor Receptor by Cultured Monocytes", *European J. of Immunology*, vol. 24, pp. 2699–2075 (1994).

Krysztopik, R. et al.,"Lazaroids Prevent Acute Cyclosporine–Induced Renal Vasoconstriction", *Transplantation*, vol. 63 (9), pp. 1215–1220 (1997).

Kucharzik, T. et al.,"Synergistic Effect of Immunoregulatory Cytokines on Peripheral Blood Monocytes from Patients with Inflammatory Bowel", *Digestive Diseases and Sciences*, vol. 42 (4), pp.805–812 (1997).

Lueng, Y. et al.,"Microencapsulation of Crystalline Insulin or Islets of Langerhans: An Insulin Diffusion Study", *Artificial Organs*, vol. 7 (2), pp. 208–212 (1983).

MacDonald, S. et al.,"Human Recombinant Histamine–Releasing Factor", *Int. Arch. of Allergy and Immunology*, vol. 113, pp. 187–189 (1997).

Nguyen, O. et al.,"Interleukin (IL)–15 is a Novel Cytokine that Induces Lymphokine–Activated Killer (LAK) Activity in Neonatal Cells", *J. of Investigative Medicine*, vol. 45 (3), pp. 241A (1997).

Patel, T. et al.,"Inhibition of Bile–Salt–Induced Hepatocyte Apoptosis by the Antioxidant Lazaroid U83836E[1]", *Toxicology and Applied Pharmacology*, vol. 142, pp. 116–122 (1997).

Roberts, R. et al., "Natural Killer (NK) Activity in Neonatal Cells: Role of Interleukin (IL)–12 and IL–15", *Journal of Investigative Medicine*, vol. 45 (3), pp. 235A (1997).

Segal, B. et al.,"Microbial Products Induce Autoimmune Disease by IL–12–Dependent Pathway", *The Journal of Immunology*, vol. 158, pp. 5087–5090 (1997).

Soon–Shiong, P. et al.,"An Immunologic Basis for the Fibrotic Reaction to Implanted Microcapsules", *Transplantation Proceedings*, vol. 23 (1), pp. 758–759 (1991).

Soon–Shiong, P. et al.,"Successful Reversal of Spontaneous Diabetes in Dogs by Intraperitoneal Microencapsulated Islets", *Transplantation*, vol. 54 (5), pp. 769–774 (1992).

Sun, A. et al.,"Microencapsulated Cells as Hormone Delivery Systems", *CRC Critical Reviews in Therapeutic Drug Carrier Systems*, vol. 4 (1), pp. 1–12 (1987).

Tanaka, H. et al.,"Lazaroid U–74500A for Warm Ischemia and Reperfusion Injury of the Canine Small Intestine", *Journal Am. coll. Surg.*, vol. 184, pp. 389–396 (1997).

Torri, C. et al.,"Synaptosomal Iron–Dependent Lipid Peroxidation Inhibition After Subarachnoid Hemorrhage by Lazaroid In Vivo Treatment", *Mol. and Chem. Neuro.*, vol. 30, pp. 15–24 (1997).

Villa, R. et al.,"Pharmacology of Lazaroids and Brain Energy Metabolism: A Review", *Pharmacological Reviews*, vol. 49 (1), pp. 99–136 (1997).

Welling, T. et al.,"Systemic Delivery of the Interleukin–1 Receptor Antagonist Protein Using a New Strategy of Direct Adenoviral–Mediated Gene Transfer to Skeletal Muscle Capillary Endothelium in the Isolated Rat Hindlimb", *Human Gene Therapy*, vol. 7, pp. 1795–1802 (1996).

Wesch, D. et al.,"Comparative Analysis of $\alpha\beta$ and $\gamma\delta$ T Cell Activation of *Mycobacterium Tuberculosis* and Isopentenyl Pyrophosphate", *Eur. J. Immun*, vol. 27, pp. 952–956 (1997).

Wong, H. et al.,"A Novel Two Step Procedure for Immobilizing Living Cells in Microcapsules for for Improving Xenograft Survival", *Biomat., Art. Cells & Immob. Biotech.*, vol. 19 (4), pp. 687–697.

Wong, H. et al.,"The Microencapsulation of Cells Within Alginate Poly–L–Lysine Microcapsules Prepared with the Standard Single Step Drop Technique: Histologically Identified Membrane Imperfections and the Associated Graft Rejection", *Biomat., Art. Cells & Immob. Biotech.*, vol. 19 (4), pp. 675–686 (1991).

Young, D.,"Inverted Microcarriers: Using Microencapsulation to Grow Anchorage–Dependent Cells", *Fundamentals of Animal Cell Encapsulation and Immobilization*, CRC Press, Chapter 11, pp. 243–265 (1993).

Young, D., et al.,"Inverted Microcarriers: Using Microencapsulation to Grow anchorage–Dependent Cells", *Biopharm*, vol. 2, pp. 34–46 (1989).

Zurawski, G. et al.,"Interleukin 13, an Interleukin 4–like Cytokine that Acts on Monocytes and B Cells, but not on T Cells", *Immunology Today*, vol. 15 (1), pp. 19–26 (1994).

\* cited by examiner

DEVICES CONTAINING CELLS OR TISSUE AND AN AGENT THAT INHIBITS DAMAGE BY A HOST CELL MOLECULE

The invention relates to inhibiting damage to donor tissue in a device in contact with a host tissue.

BACKGROUND OF THE INVENTION

Transplantation of donor tissue into a recipient can be used to treat a wide variety of disorders, including heart disease, neoplastic disease, and endocrine disease. The clinical application of transplantation-based therapies are, however, limited by several factors. These factors include immune rejection of transplanted allogeneic or xenogeneic tissue by the transplant recipient, a shortage of allogeneic donor-tissue, and donor-propagated immune attack of recipient tissue (graft-versus-host-disease).

Immune rejection of transplanted donor-tissue can be the most serious barrier to more widespread availability of the benefits of transplantation-based therapies. Implantation of allogeneic or xenogeneic donor-tissue into an immunocompetent recipient generally results in a vigorous and destructive immune response directed against the donor-graft. Efforts to prevent immune-based destruction of donor tissue have generally fallen into two categories. In one approach, efforts have been directed to moderating the recipient's immune response, e.g., by the induction of specific immunological tolerance to transplanted tissue, or much more frequently, by the administration of broad-spectrum immune suppressants, e.g., cyclosporin. In the other major approach, efforts to prolong the acceptance of a donor-graft have been directed to rendering the donor-graft less susceptible to attack, e.g., by immunoisolating the donor-tissue by encapsulating it in a way which minimizes contact of elements of the recipient's immune system with the encapsulated donor tissue.

Immunoisolation is particularly attractive for the treatment of endocrine disorders or in hormone or enzyme replacement therapies. For example, the implantation of immunoisolated pancreatic islet cells can be used to restore glucose-responsive insulin function in a diabetic recipient. Islets can be placed in a mechanical enclosure, or can be coated with a material, which allows relatively free diffusion of glucose, insulin, nutrients, and cellular waste products but which is impervious to components of the recipient's immune system.

Unless otherwise defined, all technical and scientific terms used herein have the same meaning as commonly understood by one of ordinary skill in the art to which this invention belongs. Although methods and materials similar or equivalent to those herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

SUMMARY OF THE INVENTION

A variety of devices can be used to contain a source of a therapeutic substance, often cells, which source provides the substance to a host or recipient subject. Such devices include implantable devices, of both the diffusion and perfusion types, and extra corporeal devices, e.g., those through which blood of the host or recipient is passed. In such devices, host molecules can attack the source of the therapeutic substance and impair the function of the device. The inventors have discovered that the inclusion in such a device of a rescue agent, e.g., an agent which sequesters an unwanted host cell molecule or which otherwise inhibits the activity of an unwanted host molecule, can improve the performance of the device, e.g., by extending its useful lifetime.

The inventors have discovered that the inclusion in an implantable device of a rescue agent, e.g., an agent which sequesters an unwanted host cell molecule or which otherwise inhibits the activity of an unwanted host molecule, can improve the performance of the device, e.g., by extending its useful lifetime.

Accordingly, the invention features, an implantable device which includes a source of a therapeutic substance, e.g., an islet, and a rescue agent, e.g., an antibody which binds host antibodies, disposed within a semipermeable component.

In preferred embodiments the implantable device includes a cell or tissue. The cell or tissue can be autologous, allogeneic, or xenogeneic, with regard to the subject. A xenogeneic cell or tissue can be from a species which is concordant or discordant with the subject. The cell or tissue can be from the subject, but if it is from the subject, it is preferably genetically engineered to express a substance not normally expressed by or on that cell or tissue.

In preferred embodiments the cell or tissue is from a dog, pig, goat, rabbit, horse, cow, sheep, or a non-human primate.

In preferred embodiments the cell is a pancreatic islet cell. In preferred embodiments, the pancreatic islet is from a dog, pig, goat, rabbit, horse, cow, sheep, or non-human primate. In particularly preferred embodiments, the pancreatic islet is from a pig. In preferred embodiments, the pancreatic islet is from a human other than the subject.

In preferred embodiments, the cell or tissue is genetically engineered.

The cell or tissue can be from the pancreas, adrenal gland, brain, kidney, liver, thymus, parathyroid or thyroid. In a preferred embodiment, the cell is a cultured cell. In a preferred embodiment, the cell is from a primary culture. In a preferred embodiment, the cell has been treated with a cytokine or a growth factor.

In preferred embodiments: the cell is an immortalized cell; the cell is a blood cell; the cell or tissue is a fetal cell or tissue; the cell is a skin, astroglial, or myoblast cell.

In preferred embodiments the source of a therapeutic substance (and preferably the rescue agent) is immunoisolated from the host, e.g., it is isolated from contact with one or more host immune components, e.g., antibodies or components of the complement system.

In preferred embodiments the implantable device is a perfusion device, e.g., a device through which the flow of blood is directed, e.g., intravascular devices, as e.g., in an arterial or venous shunt.

In preferred embodiments the device can be a microcapsule or a macrocapsular device, e.g., a hollow fiber, a membrane chamber, or other device which separate the source of a therapeutic substance (and preferably the rescue agent) from the host by an artificial semi-permeable barrier.

In preferred embodiments the device serves to physically contain the source of a therapeutic substance, e.g., donor cells or tissues (and preferably the rescue agent), keeping them in a contained location, at least temporarily separated from the implantation site or tissues of the host.

In preferred embodiments the device is a microcapsule or macrocapsule. It can include a gel member, e.g., a shape-retaining gel member, in which a cell or tissue is embedded. The gel can be a hydrogel. In preferred embodiments the hydrogel includes agarose, agar, collagen, polyethylene oxide (PEO), or alginate. The agarose or alginate can have a higher number of guluronic acid than mannuronic acid monomers. The microcapsule or macrocapsule can include a semipermeable membrane or coating, e.g., a semipermeable coating which surrounds a gel component, e.g. a gel core in which a cell or tissue is embedded. The semipermeable membrane can include a polymer, e.g., a positively charged polymer. By way of example, the positively charged polymer can be a polyamino acid. In preferred embodiments, the positively charged polymer includes lysine or ornithine. In a particularly preferred embodiment, the positively charged polymer is polylysine or another polymer of one or more positively charged amino acids. In preferred embodiments the coating can include chitosan.

In another aspect, the invention features, a composite microreactor which includes:

(a) one, or a plurality, of an internal particle which includes:
  (i) a source of a therapeutic substance, e.g., an islet;
  (ii) an internal particle matrix, e.g., a gel core or a solid particle, which contacts the source;
  (iii) (optionally) an internal semipermeable particle coating enclosing the internal particle matrix; and (b) a super matrix, e.g., a gel super matrix, in which the internal particle (or particles) is embedded; and (c) (optionally) an outer semipermeable coating enclosing the super matrix, the composite microreactor preferably providing a molecular weight cutoff that prevents molecules larger than about 400,000 daltons from coming into contact with the source and wherein a component of the composite microreactor, e.g., the internal particle, the super matrix, or both, are geometrically stabilized.

The composite microreactor includes one or more rescue agents.

In preferred embodiments, a rescue agent, e.g., an antibody which binds host antibodies, is disposed within one or more of an internal particle or the super matrix.

In preferred embodiments, one compartment, e.g., an internal particle, can include a first rescue agent and a second compartment, e.g., a second internal particle, or the super matrix can include a second rescue agent. E.g., one compartment can include a molecule that binds IgG, IgM, or an other host immunoglobulin, and a second compartment can include an antibody against one or more components of the complement system.

A compartment can include two or more rescue agents, e.g., an anti IgM antibody and a cytokine receptor. A rescue agent can be included in more than one compartment.

In preferred embodiments rescue agent molecules are present in more than one compartment of a composite microreactor and preferably the concentration or number of rescue agent molecules is greater in the compartment which is outermost in the microreactor. Thus, rescue agent molecules can be present in both an internal particle and in the surrounding matrix, but the concentration or number is lower in the internal particle.

In preferred embodiments an internal particle is coated with the three-part composite layer described herein.

In another aspect, the invention features a double composite microreactor which includes:

(1) one, or a plurality, of an internal particle which includes:
  (a) a source of a therapeutic substance, e.g., an islet;
  (b) an internal particle matrix which contacts the source; and
  (c) (optionally) an internal particle semipermeable coating enclosing the first internal particle matrix;

(2) one, or a plurality, of a particle which includes:
  (a) the internal particle or particles of (1)
  (b) a particle matrix in which the internal particle (or internal particles) is embedded; and
  (c) (optionally) a particle semipermeable coating enclosing the particle;

(3) a super matrix in which the particle (or particles) of (2) is embedded; and (4) (optionally) a super matrix or outer semipermeable coating, e.g., of polylysine enclosing the super matrix.

The composite microreactor includes one or more rescue agents.

In preferred embodiments, a rescue agent, e.g., an antibody which binds host antibodies, is disposed within one or more of an internal particle, a particle, or the super matrix.

In preferred embodiments, one compartment, e.g., a first internal particle, can include a first rescue agent and a second compartment, e.g., a second internal particle, or a particle, or the super matrix, can include a second rescue agent.

A compartment can include two or more rescue agents, e.g., an anti IgM antibody and a cytokine receptor.

A rescue agent can be included in more than one compartment.

In preferred embodiments rescue agent molecules are present in more than one compartment of a composite microreactor and the concentration or number of rescue agent molecules is greater in the compartment which is outer most in the microreactor. Rescue agent molecules can be present in two or more of an internal particle, a particle, or the super matrix, and the concentration or number in a compartment which is more inner is less than that in an outer compartment which includes rescue agents. In preferred embodiments: rescue agent molecules are present in an internal particle and a particle and the concentration or number is less in the internal particle; rescue agent molecules are present in an internal particle and the super matrix and the concentration or number is less in the internal particle; rescue agent molecules are present in a particle and the super matrix and the concentration or number is less in the particle.

In preferred embodiments: an internal particle is coated with the three-part composite layer described herein; a particle is coated with the three-part composite layer described herein; an internal particle and a particle are coated with the three-part composite layer described herein; an internal particle does not include the three-part layer but a particle is coated with the three-part composite layer described herein.

In another aspect, the invention features providing a subject with a therapeutic substance. The method includes implanting in the subject an implantable device which includes a source of a therapeutic substance and a rescue agent, e.g., an implantable device described herein.

In preferred embodiments the implantable device includes a cell or tissue. The cell or tissue can be autologous, allogeneic, or xenogeneic, with regard to the subject. A xenogeneic cell or tissue can be from a species which is concordant or discordant with the subject. The cell or tissue can be from the subject, but if it is from the subject, it is preferably genetically engineered to express a substance not normally expressed by or on that cell or tissue.

In preferred embodiments the subject is a human and the cell or tissue is from a second species, e.g., a discordant species, e.g., a discordant vertebrate, e.g., a dog, pig, goat, rabbit, horse, cow, sheep, or a non-human primate.

In preferred embodiments the cell is a pancreatic islet cell. In preferred embodiments, the pancreatic islet is from a dog, pig, goat, rabbit, horse, cow, sheep, or a non-human primate. In particularly preferred embodiments, the pancreatic islet is from a pig. In preferred embodiments, the pancreatic islet is from a human other than the subject.

In preferred embodiments, the cell or tissue is genetically engineered.

The cell or tissue can be from the pancreas, adrenal gland, brain, kidney, liver, thymus, parathyroid or thyroid. In a preferred embodiment the cell is a cultured cell. In a preferred embodiment, the cell is from a primary culture. In a preferred embodiment, the cell has been treated with a cytokine or a growth factor.

The inventors have discovered that the inclusion of a rescue agent in an extracorporeal device can be used to protect a source of a therapeutic substance in the extracorporeal device and improve the performance of the device, e.g., by extending its useful lifetime.

Accordingly, the invention features an extracorporeal device through which is passed a host fluid, e.g., blood. (After passage through the device the host fluid is returned to the host.) The device includes a source of a therapeutic substance, e.g., an islet, and a rescue agent, e.g., an antibody which binds host antibodies. The source is separated from the host body fluid by a semipermeable component. Preferably a semi-permeable component also separates the rescue agent from the host body fluid.

In preferred embodiments the device includes a cell or tissue. The cell or tissue can be autologous, allogeneic, or xenogeneic, with regard to the subject. A xenogeneic cell or tissue can be from a species which is concordant or discordant with the subject. The cell or tissue can be from the subject, but if it is from the subject, it is preferably genetically engineered to express a substance not normally expressed by or on that cell or tissue.

In preferred embodiments the cell or tissue is from a dog, pig, goat, rabbit, horse, cow, sheep, or a non-human primate.

In preferred embodiments the cell is a pancreatic islet cell. In preferred embodiments, the pancreatic islet is from a dog, pig, goat, rabbit, horse, cow, sheep, or a non-human primate. In particularly preferred embodiments, the pancreatic islet is from a pig. In preferred embodiments, the pancreatic islet is from a human other than the subject.

In preferred embodiments, the cell or tissue is genetically engineered.

The cell or tissue can be from the pancreas, adrenal gland, brain, kidney, liver, thymus, parathyroid or thyroid. In a preferred embodiment the cell is a cultured cell. In a preferred embodiment, the cell is from a primary culture. In a preferred embodiment, the cell has been treated with a cytokine or a growth factor.

In preferred embodiments: the cell is an immortalized cell; the cell is a blood cell; the cell or tissue is a fetal cell or tissue; the cell is a skin, astroglial, or myoblast cell.

In preferred embodiments the device includes a port for admitting flow of the body fluid into the device which port communicates with a chamber which encloses a source of a therapeutic substance, e.g., an islet, and a rescue agent, e.g., an antibody which binds host antibodies. The source, and preferably the rescue agent, are separated from the host fluid by a semipermeable component. The fluid exits the device by the same port or by a second port. The device can be used in "batch" or continuous flow fashion.

In preferred embodiments the semipermeable component includes the three-part composite layer described herein.

The methods of the invention allow implanting of allogeneic or xenogeneic tissue with little or no immunosuppression.

Unless otherwise defined, all technical and scientific terms used herein have the same meaning as commonly understood by one of ordinary skill in the art to which this invention belongs. Although methods and materials similar or equivalent to those herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

Other features and advantages of the invention will be apparent from the following detailed description and from the claims.

DETAILED DESCRIPTION OF THE INVENTION

Rescue Agents

Figure 1:
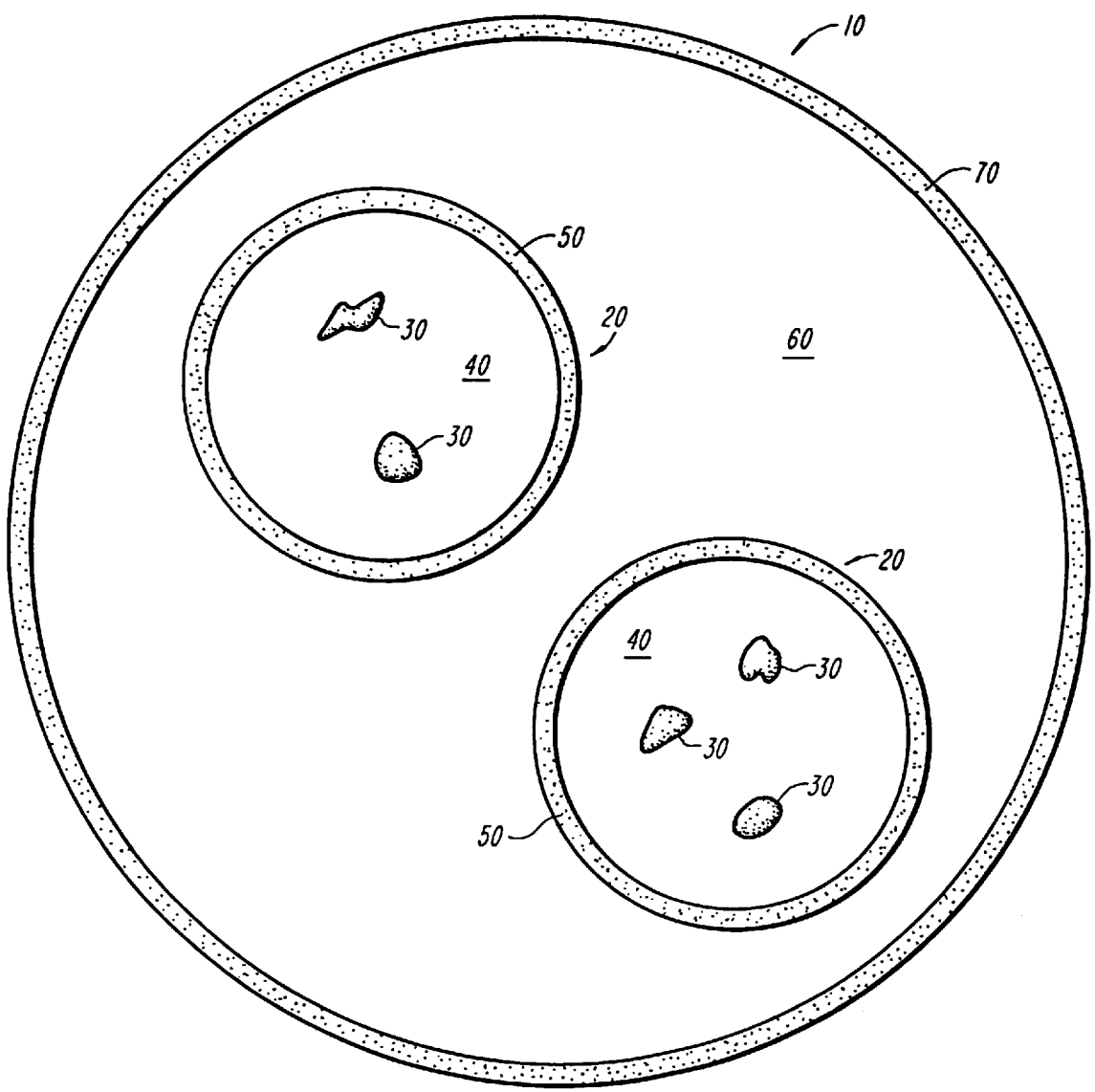
FIG. 1 is a schematic diagram of a composite microreactor.

Rescue agents are molecules (or in some cases cells) which can inhibit the ability of a host molecule to damage donor, e.g., implanted tissue. (Donor tissue is used herein to refer to tissue which is implanted into a host or recipient. Donor tissue also refers to tissue used in an extra-corporeal device, even though it is not implanted in the recipient or host.) Rescue agents can act by absorbing, adsorbing, binding, degrading, sequestering, neutralizing, or otherwise inhibiting a molecule elaborated by the host.

In the case of an implanted device, the host molecules enter the device and interact with a rescue agent within the implanted device. In other embodiments, a rescue agent is, e.g., an anti-fibrotic or an anti-macrophage agent that is released by the implanted device into the host, though in most cases the rescue agent will be contained within the device and not released.

Devices, e.g., implantable or extracorporeal devices, of the invention include a source of a therapeutic substance. The rescue agent is; a different molecule than the therapeutic substance.

A rescue agent can have a relatively high and specific affinity for a host molecule, e.g., it can have an affinity and specificity similar to that of an antibody for its antigen, an enzyme for its substrate, or a cell surface receptor for its ligand. Other rescue agents have a relatively low specificity and affinity, e.g., an affinity and specificity similar to that of protein A, protein C, or human serum albumen.

A rescue agent can be, for example, a peptide, a non-peptide molecule, or a cell. Although a rescue agent can be a cell, in preferred embodiments it is not a cell, e.g., it is a molecule.

An example of a peptide rescue agent is an antibody which binds a host molecule, for example, an antibody which binds a host antibody such as a host IgG, IgA, IgM, or IgE. The antibody can be directed against a constant region of the host antibody. The host antibody can be reactive with the source of the therapeutic substance, or for a component of the device.

An antibody rescue agent can be directed against a component of the host complement system, for example, against host C3, C3b, Factor B, Factor D, or properdin, or a host protein that activates Factor B, Factor D, or properdin.

Antibody rescue agents can also be directed against other host proteins, e.g., inflammatory molecules, e.g., inflammatory cytokincs, e.g., TNF-α, TNF-β, IL-1β, IL-6 or gamma interferon.

An antibody rescue agent can be a monoclonal antibody or a polyclonal antibody, a chimeric antibody, a humanized antibody, a single chain antibody, or a fragment derived from such antibodies.

A peptide rescue agent can be a protein which is not an antibody. A preferred embodiment of a non-antibody peptide rescue agent is an anti-inflammatory cytokine, for example, an anti-inflammatory interleukin, for example, IL-4, IL-10, or IL-13. The anti-inflammatory cytokines of the invention should be specific to the host. Other such agents include the IL-1 receptor agonist.

A non-antibody polypeptide rescue agent can be a polypeptide which binds an unwanted host molecule, reversibly or irreversibly. Examples of such rescue agent ligands can be receptors, or fragments thereof, which bind molecules elaborated by the host, e.g., host molecules which propagate an impure or inflammatory response. Preferred examples are receptors, or fragments thereof, which bind inflammatory cytokines, for example, molecules which can bind TNF-α or TNF-β, IL-1β, IL-6, or gamma interferon. Other examples of such rescue agents include: ligands which bind enzymes, for example, nitric acid synthase.

Additional rescue agents of protein or peptide nature include: a naturally-occuring or an engineered cytokine binding protein, such as TNF BP-I; an antibody to an inflammation-related enzyme, such as anti-host neutrophil myeloperoxidase; an engineered inhibitory binding protein to a host enzyme; a naturally occurring complement inhibitor such as Factor H or a soluble form of CDAF; an engineered complement binding-protein or inhibitor; or an enzyme that neutralizes an inflammatory substance, such as superoxide dismutase which reduces a superoxide anion.

A rescue agent can be naturally occurring molecule, or fragment or analog thereof, or a synthetic binding agent engineered by recombinant or protein engineering technologies. These include artificial epitope analogs, e.g., α-gal epitopes and synthesized artificial ligands, e.g., ligands discovered through phage display or other screening methods.

A rescue agent can be a non-peptide substance having an affinity for an unwanted host cell molecule, for example, a dextran blue bead or a DEAE-Affigen blue resin which has affinity for an antibody molecule. Another embodiment of a non-peptide rescue agent is an anti-inflammatory steroid, for example, a 23-amino steroid, for example a lazaroid.

A rescue agent can be a cell which produces or releases a rescue agent, for example, a peptide rescue agent discussed herein; for example, a red blood cell which can be used to rescue tissue from damaging effects or nitric oxide, or a leukocyte which produces an anti-inflammatory cytokine. A rescue agent can be an engineered cell, for example, an autologous allogeneic or xenogeneic cell engineered to release a rescue agent. In preferred embodiments where the rescue agent is a cell it is other than a red blood cell.

Rescue agents are particularly useful against host immune molecules. Molecules elaborated by the immune system which, despite the semipermeable or even immunoisolating properties of the device, can enter the device and have the effect of rejecting or being toxic to the biological material encapsulated in the device. Rejection of the tissues or cells of the biological material can be mediated by one or more components of the host immune system, such as cytokines, antibodies, complement, or other enzymes, or small molecules such as histamine. Each of these classes of agents that cause host immune rejection of implanted material can have their activity modulated by rescue agents.

A rescue agent for host immune rejection is an agent capable of protecting the encapsulated biological material from immune rejection by the host. The immune system can reject a foreign material by a variety of mechanisms involving antibody-independent pathways, such as by the action of the alternative complement pathway, or by a degranulation product of a leukocyte, for example a neutrophil. Products of neutrophil degranulation include enzymes, histamines, and reactive superoxide anions. The immune system can also reject a foreign material by an antibody-dependent process, stimulated by the binding of a molecule of an IgG, an IgM, an IgA or a molecule of another antibody isotype to an implantable device component.

Rescue agents should be non-toxic both to the biological material of the device, and to the host. The rescue agent should reduce or eliminate the activity of unwanted host molecules without substantially affecting release of the biological substance, such as insulin or thyroxin, generated by the implanted device for the benefit of the host.

In many embodiments the rescue agent is maintained within an implanted device in a stable, active form during the lifetime of the implanted device; if the rescue agent is to be released from an implanted device the pharmacokinetics of release be suitable to the kinetics of host immune rejection of the implanted device.

Further, if release from an implanted device is not desired, for example a rescue agent that is a purified preparation of a anti-IgG, for use to capture host antibody ligands, the rescue agent should be stably contained or immobilized in one or more compartments of the implanted device. This can be done by disposing semipermeable, barriers between the rescue agent and the host or by coupling the rescue agent to a component of the device.

Incorporation of anti-human antibodies into a implantable device can function as a rescue agent by binding to a host antibody molecule, e.g., a host antibody elaborated against one or more components of the implanted device, or elaborated against one or more components released by the biological material, for example, a porcine islet encapsulated in the implanted device.

As referred to above, an anti-inflammatory therapeutic agent, for example, a lazaroid (see, for example, Villa, R. et al., 1997, Pharmnacolog. Rev. 49: 999-136) can be used as a rescue agent. The lazaroid U-74500A is a 21-aminosteroid capable of inhibiting cytotoxicity and lipid peroxidation. This lazaroid reduces hydrogen peroxide generation by neutrophils and by monocytes, and can inhibit neutrophil infiltration and resultant tissue myeloperoxidase activity (Tanaka, H. et al. 1997, J. Amer. Coll. Surgeons 184: 389–396). Further, lazaroids can act synergistically with penicillamine to protect against peroxynitrite (ONOO-; Fici, G. et al., 1997, Free Radical Biol. & Med., 22: 223–228). The lazaroid U83836E protects hepatocytes from bile salt-induced apoptosis (Patel, T. et al., 1997, Toxicol. Appl. Pharmacol. 142: 116–122), and protects mesencephalic neurons from nitric oxide death (Grasbon-Frodl, E. et al., 1997, Exp. Brain Res. 113: (38–143).

Rescue agents can be provided by cells which naturally produce them or by cells which have been gradually engineered to produce the rescue agent. The cells are included in one or more compartments of an implantable device.

An example of a rescue agent-producing cell is a hybridoma cell, capable of expressing and secreting a gene encoding a rescue agent immunoglobin protein. For example, a rescue agent can be an encapsulated mouse hyridoma cell which is capable of producing an IgG molecule with affinity for an epitope on a host IgG molecule. A rescue agent can be an encapsulated cell that produces an anti-inflammatory cytokine, for example, IL-13.

Transfection and culture of cells with a gene encoding the human TNF type I receptor, or a soluble domain of this receptor, resulting in expression of a TNF binding protein (TBP-I) are disclosed in European Patent 433 900 A1. U.S. Pat. No. 5,512,544 (European Patent 512 528 A2) discloses that TBPs are useful in treatment of autoimmune diseases and graft-versus-host reactions.

Determination of Rescue Agent Suitability

An assay for implantable device glucose response can be used to determine effectiveness of a rescue agent. Porcine islet implantable devices which include the rescue agent are implanted in a suitable host, for example, a dog. Control implantable devices without the rescue agent are implanted in a similar host dog. After being implanted for a length of time sufficient for the host molecules to attack the implanted tissue, the implantable devices are removed from the host and cultured in vitro for assay of glucose response, to measure islet function and/or for standard histological staining to analyze viability, e.g., with hematoxylin and eosin. A functional islet-containing implantable devices should alter secretion of insulin in response to altered glucose concentration. For example, shift of glucose level from basal (50 mg/dl glucose) to stimulatory level (300 mg/dl) should induce a three-to six-fold increase in insulin secretion which can be sustained for one hour. Further, insulin secretion should return to basal levels after perfusion of implantable devices with basal glucose solution.

Implantable Devices

An implantable device typically includes an inner matrix, e.g., gel, e.g., a hydrogel, or core in which living cells are disposed and optionally a semipermeable coating enclosing the gel. The rescue agent can be disposed within the gel core or adhered to a coating. The coating often has a porosity which prevents components of the implant recipient's immune system from entering and destroying the cells within the implantable device. Many methods for encapsulating cells are known in the art. A few are cited below. These are cited merely as examples, and are not the only methods which can be used with the invention.

Encapsulation using a water soluble gum to obtain a semi-permeable water insoluble gel to encapsulate cells for production and other methods of encapsulation are disclosed in U.S. Pat. No. 4,352,883 issued Oct. 5, 1992.

U.S. Pat. No. 4,409,331 issued Oct. 11, 1983 discloses a process for production of substances from encapsulated cells, molecular weight cut-off of membranes, use of divalent cations for polymerization, use of various therapeutic substances, core materials, and methods of formation of the gel including cross-linkers.

Shape-retaining gelled masses that expand before membrane formation, and upon contact with chelator can be made to liquefy within the membrane, and having an optional second membrane are disclosed in U.S. Pat. No. 4,663,286 which issued May 5, 1987.

Double-membrane capsules with high molecular weight cut-offs such as 200–400 kD for the inner membrane, enabling higher density growth of encapsulated cells, and use of poly-L-lys, are disclosed in EPO Publ. No. 0301 777 of Jan. 2, 1989.

U.S. Pat. No. 5,084,350 issued Jan. 28, 1992, discloses gels reliquified within the capsule for a variety of biological samples, and materials for other implantable device components.

U.S. Pat. No. 5,427,935 issued Jun. 27, 1995, discloses composite hybrid membranes of compositions that include chitosan.

Implantable devices with multiple coatings including a halo layer, and not requiring a poly-L-lysine or other polyamino acid or polycation coating are disclosed in WO 95/19743 published Jul. 27, 1995.

Macrocapsular surfaces of decreased surface area and roughness and increased cryoprotectivity, with a variety of co-monomers and free radical initiators of polymerization, are disclosed in U.S. Pat. No. 5,545,423 which issued Aug. 13, 1996

Methods of the invention can be used with any implantable device which is suitable for delivery and maintenance of biologically active material. Such devices include gel-based implantable devices, for example, the composite implantable devices described herein and in U.S. Pat. No. 5,427,935 (Jun. 27, 1995). However, other devices can be used as well, for example, the devices described in U.S. Pat. No. 4,663,286 (May 5, 1987), particularly, the implantable devices described in U.S. Pat. No. 5,545,423 (Aug.13, 1996).

Sources of Therapeutic Substances

Implantable devices used in methods of the invention will generally include a source of a therapeutic substance, e.g., a cell or tissue. The source should release a therapeutic substance which is different from the rescue agent.

Preferably the source will be one or more living cells. Cells can be growth-inhibited, such that they do not divide, but continue to perform metabolic reactions. Growth inhibition can be achieved by one or more methods known to one with skill in the art, such as irradiation with UV light, by treatment with mitomycin, and by appropriate genetic manipulation. Exemplary cells include pancreatic islets, hepatic cells, neural cells, liver cells, renal cortex cells, vascular endothelial cells, thyroid and parathyroid cells, thymic cells, ovarian cells, blood cells, allografts or xenografts, and genetically engineered cells. Sources of cells and tissues containing cells include, without limitation, tissue or cells removed from a donor animal, tissue or cells of a primary cell culture obtained by incubation or cultivation of donor tissues and cells, cells obtained from viable cell lines and immortalized cell lines, biologically active products of cells or tissues, and the like. Cells from a primary cell line can be treated in culture with one or more cytokines or growth factors. Exemplary cells for transplantation into a subject can be from the same species as that subject, or from a different species that is discordant or concordant with the recipient subject.

In preferred embodiments the cell is an autologous cell, an allogeneic cell, or a xenogeneic cell. For example, the cell is: an autologous cell, i.e., a cell which is taken from the individual recipient into which the cell will be implanted; an allogeneic cell, i.e., a cell which is taken from a different individual of the same species as the recipient into which the cell will be implanted; a xenogeneic cell, i.e., a cell which is from a different species than the recipient into which the cell will be implanted. In the case of an allogeneic cell, the cell can be fully matched or partially matched for MHC class I loci, fully matched or partially matched for MHC class II loci, and fully matched or partially matched for minor loci. In the case of xenogeneic cells, the cells can be concordant or discordant with respect to the recipient.

In preferred embodiments the recipient animal is a dog, a pig, or a human. In preferred embodiments the donor cell is a pancreatic islet cell. In preferred embodiments: the composite implantable device contains pancreatic islets, e.g., at e.g., a density of 5,000 to 100,000 islets per milliliter of medium; the composite implantable device contains living cells at a density of about $10^4$ to $10^8$ cells per milliliter of medium.

Implantable devices used in the methods described herein can include a source of a therapeutic substance. For example, the device can Include, a composition of matter which produces or releases a therapeutic substance, e.g., a protein, e.g., an enzyme, hormone, antibody, or cytokine, a sense or anti-sense nucleic acid, e.g., DNA or RNA, or other substance which can exert a desired effect on a recipient. The source of a therapeutic substance can be a tissue or a living cell; a eukaryotic cell, e.g., a rodent, canine, porcine, or human cell; a prokaryotic cell, e.g., a bacterial cell; a fungal or plant cell; a cell which is genetically engineered, e.g., a cell which is genetically engineered to produce a protein, e.g., a human protein. The source of a therapeutic substance can be or include an autologous, an allogeneic, or a xenogeneic cell. For example, the cell is: an autologous cell, i.e., a cell which is taken from the individual recipient into which the cell will be implanted; an allogeneic cell, i.e., a cell which is taken from a different individual of the same species as the recipient into which the cell will be implanted; a xenogeneic cell, i.e., a cell which is from a different species than the recipient into which the cell will be implanted. In the case of an allogeneic cell, the cell can be fully matched or partially matched for MHC class I loci, fully matched or partially matched for MHC class II loci, and fully matched or partially matched for minor loci. In this case of xenogeneic cells, the cells can be concordant or discordant with respect to the recipient.

Implantable devices used in the methods described herein can include a composition of matter which absorbs or modifies or detoxifies a substance produced by the recipient.

Genetically modified cells can be used. This includes cells that have been modified by genetic engineering to produce a product, e.g., cells modified to overproduce a product they normally produce, as well as cells engineered to produce a produce they do not normally make. Cells which have been modified in other ways, e.g., cells modified to reduce an immune response in a subject, can also be used in methods of the invention.

Isolation of Cells

Living cells can be isolated away from surrounding tissues or grown in culture by procedures known to the art, and then suspended in a liquid medium prior to encapsulation. The living cells can provide biological substances, e.g., enzymes or co-factors, hormones, clotting factors, or growth factors. Cells, e.g., pancreatic cells, can provide enzymatic or hormonal functions. Cells such as hepatic cells can provide a detoxification function.

As an example, pancreatic islet cells were prepared from either adult mongrel dogs, pigs, or bovine calves (0–2 weeks old) by a modification of the methods of Warnock and Rajotte, *Diabetes*, 37:467 (1988), as previously described in Lanza et al., *Proc. Natl. Acad. Sci.*, 88:11100–11104 (1991).

Briefly, aseptic, viable porcine pancreata were obtained under aseptic operating room procedures. After resection (warm ischemia for less than about 15 minutes), the glands were cannulated and infused with cold (4° C.) University of Wisconsin (UW) organ preservation solution. Pancreatic tissues were dissociated using an intraductal collagenase digestion procedure. The collagenase is delivered by peristaltic pump, and the digested pancreas is mechanically disrupted in a polypropylene dissociation chamber containing 2–6 mm glass beads. The islets were separated from the exocrine tissue by discontinuous density gradient centrifugation (27%, 20.5%, and 11% (w/v) FICOLL® (Sigma, F 9378) in Eurocollins solution).

Isolated islets were then cultured for one day either in M 199/Earle's medium supplemented with 10% (vol/vol) fetal bovine serum, 30 mM HEPES, 100 milligrams/dl glucose, and 400 IU/ml penicillin (canine), or in α-MEM plus 10% heat-inactivated horse serum (bovine and porcine) in a humidified atmosphere of 5% $CO_2$/95% air at 37° C. A typical yield of islets should be in the range of $0.5-1.8 \times 10^6$ islets for adult pancreas (400 gm wet weight, islet diameter 80–125 μm, purity 85–95%, viability greater than 90%; see below). The cells can also be isolated by other procedures and cultured under other suitable conditions.

Ischemic deterioration of the islet cells is minimized by using tissue fragments of a suitable size, e.g., islet fragments should be less than about 150 microns, and preferably 50 to 125 microns, in diameter. Viability, growth, longevity, and/or function of the islet cells can be enhanced by co-culturing, i.e., by mixing other cell types in the liquid medium prior to encapsulation. Useful cell types include cells which secrete growth hormone, e.g., GH-3 cells, or cells which secrete connective tissue and/or extracellular matrix components, e.g., fibroblasts and endothelial cells. In addition, cells, e.g., islets, can be co-cultured with red blood cells, or hemoglobin, or other oxygen carrying agents can be added, to enhance oxygen availability. Red blood cells can also be used to rescue tissue from damaging effects of nitric oxide.

Islet quality control procedures are used to enable comparison of different lots of islets prepared at different times. Purity (amount of islet tissue compared to exocrine tissue contamination) can be determined by ability of pancreatic islets to rapidly take up diphenyl thiocarbazone (dithizone). Islets can be incubated for five to ten minutes with 50 micrograms/ml of dithizone (D5130, Sigma) to stain them red. The preparation is then examined under light microscopy for a qualitative estimate of purity. Quantification of purity is effected by islet dispersion and counting of stained and unstained cells, or with a spectrophotometric assay of dithizone uptake/micrograms DNA.

Viability can be determined by any one of several assays that depend on the capability of viable cells to exclude certain dyes. For example, one assay uses a combination of the fluorescent stains acridine orange, which stains only viable cells green, and propidium iodide, which stains only the nuclei of dead cells red. The islets are incubated with the dyes (acridine orange, Sigma A6014, 50 micrograms/ml, and propidium iodide, Sigma P4170, 2.5 micrograms/ml) in a PBS solution for 10 to 15 minutes and then dispersed into single cells. Counts of red and green fluorescing cells are used to calculate percent viability.

Insulin secretory activity of the islets is determined both in static culture, e.g., expressed as units of insulin per islet volume, and based on the capability of the islets to respond to graded concentrations of glucose. These values are quantitatively established by measuring the insulin secreted by islets exposed to a range of glucose concentrations, extending from 2.8 to 28 milliM glucose.

Controlled Release of Rescue Agents

Controlled release of rescue agents can be achieved by methods known in the art. U.S. Pat. No. 4,933,185 discloses microcapsules formed around a biologically-active substance in conjunction with a microcapsule core-degrading enzyme. Release occurs in a burst at a time that the molecular weight of the core is reduced to cause loss of integrity of the microcapsule.

Degradable polymeric matrices consisting of poly (L-lactic) (PLA) and nonionic pluronic TM, are disclosed in U.S. Pat. No. 5,330,768. These blends extend protein release and minimize initial protein burst.

Multiblock copolymers consisting of a hydrophilic polymer such as polyalkylene glycol or polyvinyl alcohol, and a hydrophobic polymer such as polyhydroxy butyric acid or polysiloxane, which are bioerodible, maintained in the bloodstream, and can deliver a biologically active substance are disclosed (U.S. Pat. Nos. 5,543,158 and 5,578,325). Similar compositions for delivery of a variety of therapeutic agents including cytokines are disclosed in U.S. Pat. No. .5,626,862.

Formation of Implantable Devices

Living cells, e.g., islet cells, can be encapsulated in a variety of gels, e.g., alginate, to form implantable devices, e.g., microparticles, e.g., microbeads or microspheres to physically isolate the cells once implanted into a host. To prevent entry of smaller molecular weight substances such as antibodies and complement (with a molecular weight of about 150 kDa) into these microparticles, they can be coated with a material such as poly-L-lysine, chitosan, or PAN-PVC, which provides an outer shell with a controlled pore size, or they can be treated by. e.g., cross-linking, to control their internal porosity. Alternatively, their porosity can be controlled by mixing various substances such as polyethylene oxide (PEO) directly into the gel mixture. The use of a high molecular weight molecule, e.g., a high molecular weight PEO, e.g., of about 1–8 million Da, will minimize the escape of the porosity controlling substance. Molecules of this size range can be used with or without an outer coating.

Encapsulation

The description below is directed to primarily to the formation of microcapsules, but the cells can also be incorporated into other implantable devices, e.g., implantable macroencapsulation-devices, perfusion based devices such as "hockey puck" type devices and extra corporeal devices.

Once the cells are isolated and suspended in liquid medium, they can be encapsulated by a supporting matrix, e.g., a hydrogel matrix to form a microbead, which serves as a core of an implantable device, e.g., or internal particle. The core maintains a proper cell distribution, provides strength, and enhances cell viability, longevity, and function. The core can also contribute to immunoisolation. For example, the physical distance that is created by embedding the internal particle in a supporting matrix, can provide protection from, e.g., nitric oxide and cytokines. It also protects the internal particle from direct cell-cell interactions that can elicit an undesirable host response.

Using standard techniques, a gel matrix is formed by adding cells, e.g., pancreatic islets, to a solution of nutrient medium and liquefied gel, e.g., sodium alginate, to form a suspension, and then crosslinking the gel. A rescue agent can be added at this stage. The gel matrix can be any one or a combination of a variety of substances, preferably substances that are biocompatible with the host animal, and are capable of maintaining cellular viability and physically supporting the tissue or cells in suspension.

The gels can be gelled or crosslinked, e.g., by the addition of ions such as calcium, potassium, or barium, or by a change in temperature. If temperature change is used, however, care should be taken to choose appropriate temperature changes for gelation that are not harmful or fatal to the living cells to be encapsulated. Temperature-independent gels include alginates, carrageenans, and gums such as xanthan gum. As used herein, the term alginate includes alginate derivatives. These gels should be treated using standard techniques, to remove polyphenols, lipopolysaecharides, endotoxins, and other impurities.

Alginate is composed of blocks of 1,4 linked β-D-mannuronic acid (M) and α-1-guluronic acid (G) linked together, e.g., in alternating MG blocks. The preferred alginate is one formulated with a high G block content, e.g., at least about 60 percent. The higher the percentage of G blocks in the alginate composition, the greater the pore size and the strength of the gel matrix that is obtained in the final product. In addition. alginate gels with a high M block content appear to be more immunogenic than gels with a high G block content. See, e.g., Soon-Shiong et al., *Transplant. Proc.*, 23:758–759 (1991), and Soon-Shiong et al., *Transplantation*, 54:769–774 (1992).

The gel matrix should be sufficiently viscous to maintain the cells in a dispersed state. When alginate is used as the gel matrix, it is added up to about 3%, preferably to about 1 to 2% of the liquid medium, and the solution is cross-linked to form a semisolid gel in which the cells are suspended. These percentages provide a matrix that maintains its shape and has sufficient mechanical strength to remain intact in vivo for several months.

Alginate hydrogels are preferred for the microbead cores for a number of reasons. Alginate allows rapid polymerization and immobilization of cells at room temperature using relatively benign $CaCl_2$, provides consistent gel rheology that can be conveniently varied by increasing alginate concentration, and produces microbeads with good mechanical strength.

A preferred method for making hydrogel microbeads is with an air jet.

Other methods for making hydrogel microbeads including emulsification, dripping, and the Rayleigh jet.

Controlling Pore Size of Microparticles

The pore size of the microparticles can be controlled either by applying a semipermeable shell having a particular molecular weight cutoff. This can be effected by applying an "electrostatic" coating, e.g., a coating of a polyamino acid, e.g., polylysine. Pore size can also be controlled by treating the gel matrix of the microparticles themselves to change the pore size of the matrix without any subsequent coating. E.g., the surface of the core can be altered by, e.g., cross-linking, to produce covalently modified gel matrix surface. A coating can be a formed by modifying the structure of the matrix, e.g., the matrix can be cross-linked, e.g., with metal ions, e.g., Ba or Fe ions, or by photo-cross-linking, to form an coating.

As used herein, "molecular weight cutoff" refers to the size of the largest molecule that is not substantially blocked, e.g., by a semipermeable shell or coating surrounding a microsphere or by the gel matrix itself or both. Molecules with a molecular weight above the cutoff are substantially prevented from entering or leaving the particle. The composite implantable device should generally provide a molecular weight cutoff of about 50 kDa, more preferably about 100 kDa, more preferably about 150 kDa, and most preferably about 400,000 daltons. In preferred embodiments, the molecular weight cutoff is sufficient to prevent Ig molecules, e. g., IgG, and complement, from entering and coming into contact with the encapsulated material.

Altering the Pore Size of the Gel Matrix

The pore size of the gel matrix can be altered in several ways. For example, the gel matrix can be altered, e.g., the porosity can be either increased or decreased so as to influence the transport properties, e.g., permeability and/or molecular weight cutoff, by adding, e.g., gelatin, or collagen, or barium, or other ions with the same valance as $Ca^{++}$ions. Changes in the temperature will also affect the pore size. An increase in the temperature will result in shrinkage of the gel matrix. The addition of compound, e.g., PEO, to the gel matrix can also result in altered pore size. PLO can act to repel protein and to hinder fibrotic response. In preferred embodiments, PEO of molecular weight greater than 1,000 kDa, more preferably greater than 4,000 kDa, and most preferably greater than 8,000 kDa, is mixed with the gel matrix. PEO of relatively high molecular weight will not diffuse out and thus does not require crosslinking.

Coating with Polylysine

To coat an alginate core with polylysine the alginate core is dropped into a solution of 0.05% polylysine in serum free culture medium. The thickness of the polylysine coating can be increased by increasing the time the alginate core is left in the solution, or alternatively, by increasing the concentration of the solution. The volume of beads to solution can be, e.g., 1:5, 1:10, or 1:20. For smaller beads a greater proportion of solution is desirable.

Coatings Which Minimize Particle Volume

Embodiments of the invention use coatings which reduce the volume of a component, e.g., a core, to which they are applied. For example, a polyaminoacid coating, e.g., a polylysine, or polyornithine made from a polyaminoacid of a relatively low molecular weight, can result in a significant reduction in the volume of a gel core, e.g., an alginate core, to which it is applied. In many cases the reduction in volume is as much as about 50%, or even 60–70%, or more.

Relatively low molecular weight, as used herein, means about 30,000 Da or less, more preferably about 15 kDa or less, more preferably about 10 kDa or less, more preferably about 8 kDa or less, more preferably about 7 kDa or less, more preferably about 5 kDa or less, more preferably about 4 kDa or less, more preferably about 3 kDa or less, and most preferably about 1.5 kDa or less.

For example, the use of polylysine of a relatively low molecular weight, e.g., 3, 7, or 9.6 kDa, can result in a significant reduction, (approximately 30% in some cases) in the diameter, of the core to which it is applied. In addition to the decrease in volume, the use of a low molecular weight polyamino acid will result in a coat having superior permselective properties. However, the use of a low molecular weight polyaminoacid often results in a surface which is "pruned", i.e., relatively convoluted or rough, and which can elicit a fibrotic response. The composite implantable device of the invention, by using this coating on the internal particle, and a smooth surface, e.g., of alginate, oil the exterior of the composite implantable device, can obtain the benefits of a coating of relatively low molecular weight and also inhibit fibrosis.

The permselectivity properties of a poly amino acid, e.g., a polylysine, coating improve after the coating has been aged 2 or more hours. Thus, for best results, particles coated with these coatings should not be implanted in recipients until the coating has aged.

Geometric Stabilization

Some particles or components are not geometrically stable immediately after manufacture, e.g., the particle or component can change size or shape. If internal particles which are incorporated into a composite implantable device change geometry, the components of the composite implantable device, e.g., the super matrix or outer coating, can be damaged and the integrity of the composite implantable device can be compromised. Although not wishing to be bound by theory, the inventors believe that changes in the geometry can damage the super matrix or the outer coating, e.g., by inducing fissures or discontinuities. Damaged particles can allow the fibrotic proliferation of recipient cells on the inner particles when implanted into a recipient. Therefore, it is often desirable to geometrically stabilize internal particles, preferably prior to incorporating them into composite implantable devices. Stabilization can generally be accomplished by allowing the particles to "age" for a short time before incorporation into larger structures. The aging should be done under condition which maximizes the viability of encapsulated cells. Geometric stabilization is particularly important when the particles are coated with a relatively low molecular weight poly-amino acid.

Polylysine-coated alginate particles, especially those coated with relatively low molecular weight polylysine, should be geometrically stabilized. The polylysine coated alginate particles should be placed in a culture medium, suitable for the cell being used, and allowed to stabilize overnight. Geometric stabilization methods taught in PCT/US96/03135 and U.S. patent application Ser. No. 08/402, 209, Filed Mar. 10, 1995, can be used with methods and devices of the invention.

Improved Three-part Composite Semipermeable Coatings

The inventors have discovered a particularly efficacious semipermeable coating to be used in devices of the invention, in particular implantable devices, and in particular microreactors.

Accordingly, in another aspect, the invention features, a semipermeable coating which includes a first, or innermost layer of a polyamino acid; an intermediate gel component, which can be a thin discrete layer but more preferably is integrated into one or both of the polyamino acid layers; and a second or outermost layer of a polyamino acid. This coating is referred to herein as a three-part composite layer. Preferably the layers are adjacent to one another in contact and are not spaced apart. In preferred embodiments the polyamino acid layers are within 10, 5 or 1 or 2 $\mu m$ of each other and are more preferably in contact with one another.

The molecular weight of the inner layer of polyamino acid should be chosen such that it is lower than the molecular weight of the outer layer of polyamino acid. Preferably, the inner most layer is in the range of 1–5 kd, more preferably 2–4 kd. In preferred embodiments the molecular weight is about 2 or 3.9. (The molecular weight can be determined by as average molecular weight by viscosity or by Lall's method). Generally the inner layer is chosen to optimize permselectivity, e.g., the ability to exclude IgG. Generally, lowering the molecular weight improves selectivity. However, the use of relatively low molecular weights also have disadvantages, e.g., the use of low molecular weight coatings can result in mechanical instability and the induction of faults or fissures in other components of the microreactor, e.g., in the matrix or super matrix of a microreactor. Such fissures or faults can allow the development of fibrotic proliferation on the surface an internal particle or a particle which has induced faults in the surrounding matrix or super matrix. The disadvantages accompanying the use of such low molecular weight coatings can be overcome by adding to additional members or components to the coating, an intermediate alginate member and second, outermost coating of a polyamino acid. The molecular weight of the inner layer of polyamino acid should sufficiently small that without the other two members of the three part layer it would induce faults in a surrounding matrix.

The intermediate member, is a gel, e.g., alginate. It is an electrostatic component which often does not form a discrete layer between the two polyamino acid layers but rather integrates into the two. If a discreet layer is formed it is thin, e.g., it is no more than 10, more preferably no more than 5, or 1 or 2 μm in thickness. The gel should be such that it can electrostatically saturate the underlying polyamino acid layer and does not exceed the thickness limitations described herein.

The outer layer of polyamino acid has a higher molecular weight than the inner layer. While molecular weight is minimized in the first layer to maximize permselectivity, a higher molecular weight is used in the outer layer to promote mechanical stability and to prevent the induction of fissures or faults in the surrounding gel matrix or supermatrix. In preferred embodiments the molecular weight is between 5 and 15 and more preferably between 5–15, 8–12, and 9–10 kd. In particularly preferred embodiments the molecular weight is about 9 kd. The molecular weight of the outer layer of polyamino acid should sufficiently large that in combination with the other two elements, faults are not induced a surrounding matrix.

In preferred embodiments the coating includes an inner layer of polyamino acid, preferably polylysine, of about 2–4 kd; an intermediate gel member, preferably alginate, which integrates into the inner polyamino acid layer; an outer layer of a polyamino acid, preferably, polylysine, of about 8–12 kd.

This three-part composite layer can be used on any of the devices described herein. In preferred embodiments the three-part composite layer coats: an internal particle of a single composite microreactor; an internal particle of a double composite microreactor; a particle of a double composite microreactor; an internal particle and a particle of a double composite microreactor.

Composite Microreactors Which Include Rescue Agents

The inventors have discovered that composite microreactors which include rescue agents are particularly useful to immunoisolate donor cells. Composite microreactors which include rescue agents allow donor cells, e.g., porcine, bovine, canine, or human islet cells to be successfully transplanted into a recipient animal, e.g., mouse, rat, dog, or human with little or no need for immunosuppressant or anti-fibrotic drugs. Composite microreactors can be made by the methods taught in PCT/US96/03135 and U.S. Pat. application Ser. No. 8/402,209, Filed Mar. 10, 1995.

Accordingly, in one aspect, the invention features, a composite microreactor which includes:

(a) one, or a plurality, of an internal particle which includes:
  (i) a source of a therapeutic substance, e.g., an islet;
  (ii) an internal particle matrix, e.g., a gel core or a solid particle, which contacts the source;
  (iii) (optionally) an internal semipermeable particle coating enclosing the internal particle matrix; and (b) a super matrix, e.g., a gel super matrix, in which the internal particle (or particles) is embedded; and (c) (optionally) an outer semipermeable coating enclosing the super matrix, the composite microreactor preferably providing a molecular weight cutoff that prevents molecules larger than about 400,000 daltons from coming into contact with the source and wherein a component of the composite microreactor, e.g., the internal particle, the super matrix, or both, are geometrically stabilized.

The composite microreactor includes one or more rescue agents.

In preferred embodiments, a rescue agent, e.g., an antibody which binds a host antibody, is disposed within one or more of an internal particle or the super matrix.

In preferred embodiments, one compartment, e.g., an internal particle, can include a first rescue agent and a second compartment, e.g., a second internal particle, or the super matrix can include a second rescue agent. E.g., one component can include a molecule that binds IgG, IgM, or an other host immunoglobulin, and a second compartment can include an antibody against one or more components of the complement system.

A compartment can include two or more rescue agents, e.g., an anti-IgM antibody and a cytokine receptor. A rescue agent can be included in more than one compartment.

In preferred embodiments rescue agent molecules are present in more than one compartment of a composite microreactor and preferably the concentration or number of rescue agent molecules is greater in the compartment which is outer most in the microreactor. Thus, rescue agent molecules can be present in both an internal particle and in the surrounding matrix, but the concentration or number is lower in the internal particle.

In preferred embodiments: an internal particle is coated with the three-part composite layer described herein.

In preferred embodiments the internal particle matrix is or includes: a gel, e.g., a hydrogel, e.g., an alginate or agarose gel; a solid particle, e.g., a glass bead; a particle having pores or interstices. In preferred embodiments the internal particle matrix is other than a liquid. The internal particle matrix can include substances which impede the passage of recipient-derived molecules or cells, e.g., it can include polyethylene oxide (PEO), polystyrene sulfonic acid (PSA), or polyornithine (PLO). In preferred embodiments, a rescue agent is disposed within the internal particle matrix.

In preferred embodiments the internal particle matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement.

In preferred embodiments the internal particle coating is or includes: a polyaminoacid, e.g., polylysine (PLL) or PLO; a naturally occurring substance, e.g., chitosan; a synthetic polymer e.g., PAN-PVC. A particularly preferred coating is polyamino acid. e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa, about 1 kDa-less than 4 kDa, e.g., 3.7 kDa, or about 5 kDa to less than about 15 kDa, or about 5 kDa to less than about 10 kDa, e.g., 9 kDa–10 kDa, e.g., 9.7 kDa. Also preferred are polyaminoacid, e.g., PLL or PLO, coatings in the range of 1 or 2–10 kD, preferably in the range of 1–2, 1–3, or 1–4 kD. Preferred coatings are volume-reducing coatings.

In preferred embodiments the internal particle coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the super matrix is or includes: a gel, e.g., a hydrogel, e.g., an alginate or agarose gel. In preferred embodiments the super matrix is other than a liquid. The super matrix can include substances which impede the passage of recipient-derived molecules or cells, e.g., it can include polyethylene oxide (PEO), polystyrene sulfonic acid (PSA), or polyornithine (PLO). A high molecular weight, molecule, e.g., a polymer, e.g., PEO, with a molecular weight of 1–8 million daltons, or more, can be added to the super matrix to confer immunoisolating properties.

In preferred embodiments a rescue agent is disposed within the super matrix.

In preferred embodiments the super matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the super matrix has little or no ability to exclude low molecular weight species, e.g., IgG or complement, with this property being relegated to other components of the microcapsule.

In preferred embodiments the outer coating (which is optional) is or includes: a polyaminoacid, e.g., polylysine (PLL) or PLO; a naturally occurring substance, e.g., chitosan. A particularly preferred coating is polyamino acid, e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa (or about 1 kDa–less than 4 kDa) e.g., 3.7 kDa, or about 5 kDa to less than 15 kDa, or about 5 kDa to less than about 10 kDa, e.g., 9 kDa–10 kDa, e.g., 9.7 kDa. Also preferred are polyaminoacid, e.g., PLL or PLO, coatings in the range of 1 or 2–10 kD, preferably in the range of 1–2, 1–3, or 1–4 kD.

In preferred embodiments the outer coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the diameter of the internal particle, before application of a volume-reducing coating, is between 50 and 700 microns, more preferably between 100 and 500 microns, more preferably between 200 and 400 microns, and most preferably about 300 microns in diameter. The diameter of the internal particles, after application of a volume-reducing coating, is preferably between 35 and 500 microns, more preferably between 75 and 400 microns, more preferably between 100 and 300 microns, and most preferably about 200 microns in diameter.

In preferred embodiments the diameter of the composite microreactor is between 100 microns and 4 millimeters, between 300 and 1200 microns, between 300 and 1500 microns, between 400 and 1000 microns, or between 400 and 800 microns. More preferably the diameter is about 600 microns.

In preferred embodiments the composite microreactor includes a plurality of internal particles, e.g., between 2 and 100, e.g., 2 and 10, internal particles.

In preferred embodiments the composite microreactor is a component of a higher order composite, e.g., a double composite, or a third order composite.

In preferred embodiments one or more components of the composite is geometrically stabilized, as is taught in PCT/US96/03135 and U.S. patent application Ser. No. 08/402,209, Filed Mar. 10, 1995. For example: the internal particle matrix is geometrically stabilized, e.g., by allowing it to age for between 2 hours and 14 days, e.g., for between 12 hours and 4 or 5 days, prior to coating it; the internal particle is geometrically stabilized, e.g., by allowing it to age for between 2 hours and 14 days, e.g., for between 12 hours and 4 or 5 days prior to embedding it in the super matrix.

In preferred embodiments the internal particle coating has a lower molecular weight exclusion number than does the super matrix, the outer coating (if present), or the combination of the super matrix and the outer coating, e.g., the internal particle coating excludes recipient immune molecules, e.g., IgG or complement, and the super matrix, the outer coating (if present), or the combination of the super matrix and the outer coating, allows immune molecules, e.g., IgG or complement, to pass but excludes the passage of recipient cells.

In preferred embodiments: the outer surface of the composite is biologically compatible, e.g., it is sufficiently smooth that it inhibits fibrotic encapsulation of the composite; the outer surface of the composite is biologically compatible, e.g., it is sufficiently smooth that it inhibit fibrotic encapsulation of the composite but the surface of the internal particle is not biologically compatible, e.g., it is not sufficiently smooth to inhibit fibrotic encapsulation.

In preferred embodiments: at least one of the super matrix and the outer coating prevents contact of fibrotic cells with the internal particle coating.

In preferred embodiments the composite microreactor further includes:

(b) one, or a plurality, of a second internal particle which includes:
  (i) a second source of a therapeutic substance, e.g., an islet or a cell other than and islet;
  (ii) a second internal particle matrix which includes the second source,
  (iii) (optionally) a second internal particle coating enclosing the second internal particle;

In preferred embodiments: super matrix prevents contact of fibrotic cells with the internal particle coating; the super matrix and the outer coating (if present) is free of defects which arise from the inclusion of non-geometrically stabilized components, e.g., non-geometrically stabilized internal particles; at least two, or three, or four, components chosen from the group of the internal particle matrix, the internal particle coating, the super matrix, and the outer coating (if present), provides a molecular weight cutoff that prevents molecules larger than about 150,000 daltons from coming into contact with the sources; the internal particle molecular weight cutoff is provided by a pore structure of the internal particle matrix, and that pore structure results, e.g., from cross-linking of the internal particle gel; the molecular weight cutoff the super matrix is provided by a pore structure of the super matrix.

Preferred embodiments lack an outer coating.

In preferred embodiments the outer surface of the composite microreactor is a gel, e.g., an alginate gel. In more preferred embodiments the outer surface of the composite microreactor is a gel, e.g., an alginate gel, the outer surface of which has been modified, e.g., by cross-linking, to produce a covalently modified gel surface, e.g., to form a coating.

In preferred embodiments the outer component of the composite microreactor, i.e., the component in contact with the recipient, is at least 50, 75, 90, 95, 97, or 98%, water.

In preferred embodiments one or more components of the composite microreactor is of sufficient diameter, or of sufficient thickness, such that it imposes a substantial distance (or separation) between recipient cells, e.g., lymphocytes, macrophages, or NK cells, and the source of a therapeutic substance. In more preferred embodiments the thickness (e.g., the distance between its inner surface and its outer surface) of a component, e.g., a matrix, e.g., a particle matrix or super matrix, is: at least 5, 10, 20, 50, 75, 100, or 200 microns. In more preferred embodiments the distance between recipient cells and the source of a therapeutic substance is: at least 5, 10, 20, 50, 75, 100, or 200 microns; sufficient such that exposure of the source of a therapeutic substance to small molecules (e.g., molecules which are not excluded by a component which excludes IgG, e.g., cytokines, nitric oxide (NO), and other toxic moieties) released by recipient cells is substantially reduced (e.g., by diffusion), e.g., reduced at least 10, 20, 50, 75, or 90%; sufficient such that the concentration of small molecules (e.g., molecules which are not excluded by the semipermeable barrier-components of the composite microreactor, e.g., cytokines, NO, and other toxic moieties) released by recipient cells is substantially reduced (e.g., by diffusion), e.g., reduced at least 10, 20, 50, 75, or 90% at the source of a therapeutic substance. In more preferred embodiments: the distance is supplied by one or both of the particle matrix and the super matrix.

In preferred embodiments one or more components of the composite microreactor is of sufficient diameter, or of sufficient thickness, such that it imposes a substantial distance (or separation) between recipient cells, e.g., lymphocytes, macrophages, or NK cells, and one or both of the source of a therapeutic substance or donor antigen (other than the therapeutic substance) released by the source (e.g., donor proteins, which could stimulate a recipient response against donor tissue). In more preferred embodiments the thickness (e.g., the distance between its inner surface and its outer surface) of a component, e.g., a matrix, e.g., a particle matrix or super matrix, is: at least 5, 10, 20, 50, 75, 100, or 200 microns. In more preferred embodiments the distance between recipient cells and the source of a therapeutic substance is: at least 5, 10, 20, 50, 75, 100, or 200 microns; sufficient such that the amount, number, or concentration of a donor antigen, released into the recipient, or contacting recipient cells, is substantially reduced (e.g., by diffusion, or by trapping in or exclusion by the component or components which supply the separation), e.g., reduced by at least 10, 20, 50, 75, or 90%; sufficient such that contact of cells of the recipient with donor antigens, e.g., proteins, which protrude from or extend through the internal particle matrix or internal particle coating, or both, is substantially reduced (e.g., by diffusion, or by trapping in or exclusion by the component or components which supply the separation), e.g., reduced by at least 10, 20, 50, 75, or 90%; sufficient to inhibit acute release of donor antigens. In more preferred embodiments: the distance or separation is supplied by one or both of the particle matrix and the super matrix.

The inventors have discovered that a single or simple composite microreactor, e.g., one which includes one or more microcapsules contained in a larger particle, and which include a rescue agent, can be used to immunoisolate donor tissue. They have further discovered that higher order composites, e.g., double composites, which include one or more single composites contained in a larger particle, and which include a rescue agent, are also effective for immunoisolating donor tissue.

Accordingly, the invention features, a double composite microreactor which includes:

(1) one, or a plurality, of an internal particle which includes:
   (a) a source of a therapeutic substance, e.g., an islet;
   (b) an internal particle matrix which contacts the source; and
   (c) (optionally) an internal particle semipermeable coating enclosing the first internal particle matrix;
(2) one, or a plurality, of a particle which includes:
   (a) the internal particle or particles of (1)
   (b) a particle matrix in which the internal particle (or internal particles) is embedded; and
   (c) (optionally) a particle semipermeable coating enclosing the particle;
(3) a super matrix in which the particle (or particles) of (2) is embedded; and
(4) (optionally) a super matrix or outer semipermeable coating, e.g., of polylysine enclosing the super matrix.

In preferred embodiments the internal particle matrix is or includes: a gel, e.g., a hydrogel, e.g., an alginate or agarose gel; a solid particle, e.g., a glass bead; a particle having pores or interstices. In preferred embodiments the internal particle matrix is other than a liquid. The internal particle matrix can include substances which impede the passage of recipient-derived molecules or cells, e.g., it can include polyethylene oxide (PEO), polystyrene sulfonic acid (PSA), or polyornithine (PLO).

The composite microreactor includes one or more rescue agents.

In preferred embodiments, a rescue agent, e.g., an antibody which binds a host antibody, is disposed within one or more of an internal particle, a particle, or the super matrix.

In preferred embodiments, one compartment, e.g., an internal particle, can include a first rescue agent and a second compartment, e.g., a second internal particle, or a particle matrix, or the super matrix, can include a second rescue agent.

A compartment can include two or more rescue agents, e.g., an anti IgM antibody and a cytokine receptor.

A rescue agent can be included in more than one compartment.

In preferred embodiments rescue agent molecules are present in more than one compartment of a composite microreactor and the concentration or number of rescue agent molecules is greater in the compartment which is outer most in the microreactor. Rescue agent molecules can be present in two or more of an internal particle, a particle, or the super matrix, and the concentration or number in a compartment which is more inner is less than that in an outer compartment which includes rescue agents. In preferred embodiments: rescue agent molecules are present in an internal particle and a particle and the concentration or number is less in the internal particle; rescue agent molecules are present in an internal particle and the super matrix and the concentration or number is less in the internal particle; rescue agent molecules are present in a particle and the super matrix and the concentration or number is less in the particle.

In preferred embodiments: an internal particle is coated with the three-part composite layer described herein; a particle is coated with the three-part composite layer described herein; an internal particle and a particle are coated with the three-part composite layer described herein; an internal particle does not include the three-part layer but a particle is coated with the three-part composite layer described herein.

In preferred embodiments cells which produce a therapeutic substance, e.g., islet cells, are disposed in an internal particle and a rescue agent, e.g., an antibody, is disposed in the internal particle or in the super matrix.

In preferred embodiments the internal particle matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments a rescue agent is disposed within the internal particle matrix.

In preferred embodiments the internal particle coating is or includes: a polyaminoacid, e.g., polylysine (PLL) or PLO; a naturally occurring substance, e.g., chitosan; a synthetic polymer e.g., PAN-PVC. A particularly preferred coating is polyamino acid. e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa, about 1 kDa-less than 4 kDa. e.g., 3.7 kDa, or about 5 kDa to less than 15 kDa, or about 5 kDa to less than about 10 kDa, e.g., 9 kDa–10 kDa, e.g., 9.7 kDa. Also preferred are polyaminoacid, e.g., PLL or PLO, coatings in the range of 1 or 2–10 kD, preferably in the range of 1–2, 1–3, or 1–4 kD. Preferred coatings are volume-reducing coatings.

In preferred embodiments the internal particle coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the diameter of the internal particle, before application of a volume-reducing coating, between 50 and 700 microns, more preferably between 100 and 500 microns, more preferably between 200 and 400 microns, and most preferably about 300 microns in diameter. The diameter of the internal particles, after application of a volume-reducing coating, is preferably between 35 and 500 microns, more preferably between 75 and 400 microns, more preferably between 100 and 300 microns, and most preferably about 200 microns in diameter.

In preferred embodiments the particle matrix is or includes: a gel, e.g., a hydrogel, e.g., an alginate or agarose gel. In preferred embodiments the particle matrix is other than a liquid. The particle matrix can include substances which impede the passage of recipient-derived molecules or cells, e.g., it can include polyethylene oxide (PEO), polystyrene sulfonic acid (PSA), or polyornithine (PLO).

In preferred embodiments a rescue agent is disposed within the particle matrix.

In preferred embodiments the particle matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the particle coating is or includes: a polyaminoacid, e.g., polylysine (PLL) or PLO; a naturally occurring substance, e.g., chitosan; a synthetic polymer e.g., PAN-PVC. A particularly preferred coating is polyamino acid. e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa. Also preferred are polyaminoacid, e.g., PLL or PLO, coatings in the range of 1 or 2–10 kD, preferably in the range of 1–2, 1–3, or 1–4 kD. Preferred coatings are volume-reducing coatings.

In preferred embodiments the particle coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the diameter of the particle, before application of a volume-reducing coating, is between 200 and 1,000 microns, more preferably between 400 and 800 microns, more preferably between 500 and 700 microns, and most preferably about 600 microns in diameter. The diameter of the particles, after application of a volume-reducing coating, is preferably between 100 and 700 microns, more preferably between 250 and 550 microns, more preferably between 300 and 500 microns, and most preferably about 400 microns in diameter.

In preferred embodiments the super matrix has little or no ability to exclude low molecular weight species, e.g., IgG or complement, with this property being relegated to other components of the microcapsule.

In preferred embodiments a rescue agent is disposed within the super matrix.

In preferred embodiments the gel super matrix is or includes: a hydrogel, e.g., an alginate or agarose gel. In preferred embodiments the super matrix is other than a liquid. The super matrix can include substances which impede the passage of recipient-derived molecules or cells, e.g., it can include polyethylene oxide (PEO), polystyrene sulfonic acid (PSA), or polyornithine (PLO). A high molecular weight, molecule, e.g., a polymer, e.g., PEO, with a molecular weight of 1–8 million daltons, or more, can be added to the super matrix to confer immunoisolating properties.

In preferred embodiments the super matrix hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the super matrix has little or no ability to exclude low molecular weight species, e.g., IgG or complement, with this property being relegated to other components of the microcapsule.

In preferred embodiments the super matrix coating (which is optional) is or includes: a polyaminoacid, e.g., polylysine (PLL) or PLO; a naturally occurring substance, e.g., chitosan. Particularly preferred coating is polyamino acid. e.g., polylysine or polyornithine, having a molecular weight of less than 15 kDa, more preferably of less than 10 kDa, more preferably of less than 5 kDa. Particularly preferred are polyamino acids, e.g., polylysines, with a molecular weight of about 1 kDa–4 kDa (or about 1 kDa-less than 4 kDa) e.g., 3.7 kDa, or about 5 kDa to less than 15 kDa, or about 5 kDa to less than about 10 kDa, e.g., 9 kDa–10 kDa, e.g., 9.7 kDa. Also preferred are polyaminoacid, e.g., PLL or PLO, coatings in the range of 1 or 2–10 kD, preferably in the range of 1–2, 1–3, or 1–4 kD.

In preferred embodiments the particle coating hinders the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells.

In preferred embodiments the diameter of the double composite microreactor is, before application of a volume-reducing coating, between 400 and 1,500 microns, more preferably between 500 and 1,300 microns, more preferably between 600 and 1,100 microns, and most preferably about 900 microns in diameter. The diameter of the double composite microreactor is, after application of a volume-reducing coating, is preferably between 300 and 1,300 microns, more preferably between 400 and 1,200 microns, more preferably between 500 and 1,000 microns, and most preferably about 800 microns in diameter.

In preferred embodiments the composite microreactor includes a plurality of internal particles, e.g., between 2 and 100, e.g., between 2 and 10, internal particles.

In preferred embodiments the composite microreactor includes a plurality of particles, e.g., between 2 and 100, e.g., 2 and 10, particles.

In preferred embodiments the double composite microreactor is a component of a higher order composite, e.g., a third or fourth order composite.

In preferred embodiment one or more components of the composite is geometrically stabilized, as is taught in PCT/US96/03135 and U.S. patent application Ser. No. 08/402, 209, Filed Mar. 10, 1995. For example: the first internal particle matrix is geometrically stabilized, e.g., by allowing it to age for between 2 hours and 14 days, e.g., for between 12 hours and 4 or 5 days, prior to coating it; the first internal particle is geometrically stabilized, e.g., by allowing it to age for between 2 hours and 14 days, e.g., for between 12 hours and 4 or 5 days prior to embedding it in the particle matrix; the first particle matrix is geometrically stabilized, e.g., by allowing it to age for between 2 hours and 14 days, e.g., for between 12 hours and 4 or 5 days, prior to coating it; the first particle is geometrically stabilized, e.g., by allowing it to age for between 2 hours and 14 days, e.g., for between 12 hours and 4 or 5 days prior to embedding it in the super matrix; the super matrix is geometrically stabilized, e.g., by allowing it to age for between 2 hours and 14 days, e.g., for between 12 hours and 4 or 5 days prior to coating it; the coated super matrix is geometrically stabilized, e.g., by allowing it to age for between 2 hours and 14 days, e.g., for between 12 hours and 4 or 5 days.

In preferred embodiments the internal particle coating has a lower molecular weight exclusion number than does the particle matrix, the super matrix, the outer coating (if present), or a combination of one or more of these, e.g., the internal particle coating excludes recipient immune molecules, e.g., IgG or complement, and the particle matrix, super matrix, the outer coating (if present), or a combination of these, allows immune molecules, e.g., IgG, or complement, to pass but excludes the passage of recipient cells.

In preferred embodiments: the outer surface of the composite is biologically compatible, e.g., it is sufficiently smooth that it inhibits fibrotic encapsulation of the composite; the outer surface of the composite is biologically compatible, e.g., it is sufficiently smooth that it inhibit fibrotic encapsulation of the composite but the surface of the internal particle (or of the particle) is not biologically compatible, e.g., it is not sufficiently smooth to inhibit fibrotic encapsulation.

In preferred embodiments: the first source is an islet; the second source is an islet; the third source is an islet; the fourth source is an islet; one source is an islet and another source is other than an islet, e.g. an erythrocyte, an acinar cell, or an adrenal cell.

In preferred embodiments: an internal particle coating is a low molecular weight polyamino acid e.g., 1 kDa–4 kDa, about 1 kDa-less than 4 kDa and a particle coating is a low molecular weight polyamino acid e.g., 5 kDa to less than about 10 kDa, 5 kDa to less than about 15 kDa, e.g., about 9 kDa–10 kDa. Also preferred are polyaminoacid, e.g., PLL or PLO, coatings in the range of1 or 2–10 kD, preferably in the range of 1–2, 1–3, or 1–4 kD.

In preferred embodiments: an internal particle coating has an exclusion limit of about 150 kDa and the first particle coating has an exclusion limit of about 400 kDa.

In preferred embodiments: an internal particle coating has an exclusion limit of about 150 kDa and the particle matrix, first particle coating, super matrix, outer coating, or a combination thereof, has an exclusion limit of about 400 kDa.

In preferred embodiments: an internal particle coating has an exclusion limit which is lower than that of the particle coating, e.g., the internal particle coating has an exclusion limit which will exclude molecules which are the size of IgG, or C1q, or larger, and the particle coating has an exclusion limit which, though permeable to IgG, or C1q, will exclude objects, e.g., cells, having a molecular weight of one million or more.

In preferred embodiments: an internal particle coating has an exclusion limit which is lower than that of the particle coating, e.g., the internal particle coating has an exclusion limit which will exclude molecules which are the size of IgG, or C1q, or larger, and the particle matrix, first particle coating, super matrix, outer coating, or a combination thereof, has an exclusion limit which, though permeable to IgG, or C1q, will exclude objects, e.g., cells, having a molecular weight of one million or more.

In preferred embodiments: there is a buffer-zone component, e.g., the particle matrix, which is disposed between a component which is not biocompatible, e.g., which is not anti fibrotic, e.g., the internal particle coating, and a component which has an exclusion limit which excludes the passage of recipient cells, e.g., the super matrix or outer coating.

In preferred embodiments: an internal particle coating has an exclusion limit which will exclude molecules which are the size of IgG, or C1q, or larger, the particle matrix is not free of defects which arise from the use of non-geometrically stabilized components, and the super matrix, outer coating, or a combination thereof, has an exclusion limit which, though permeable to IgG, or C1q, will exclude objects, e.g., cells, having a molecular weight of one million or more.

In preferred embodiments, the first particle of the double composite microreactor further includes:
  one, or a plurality, of a second internal particle which includes:
    (i) a second source of a therapeutic substance, e.g., an islet;
    (ii) a second internal particle matrix which contacts the second source;

(iii) a second internal particle coating enclosing the second internal particle matrix;

In preferred embodiments, the double composite microreactor further includes:

one, or a plurality, of a second particle which includes:
(a) a third internal particle which includes:
(i) a third source of a therapeutic substance, e.g., an islet,
(ii) a third internal particle matrix which contacts the third source,
(iii) (optionally) a third internal particle coating enclosing the third internal particle matrix; and
(b) (optionally) a fourth internal particle which includes:
(i) a fourth source of a therapeutic substance, e.g., an islet,
(ii) a fourth internal particle matrix which contacts the fourth source,
(iii) a fourth internal particle coating enclosing the fourth internal particle matrix.

In preferred embodiments: one or more of the particle matrix, particle covering, or super matrix, prevents contact of fibrotic cells with the internal particle coating; the particle matrix, super matrix or the outer coating (if present) is free of defects which arise from the inclusion of non-geometrically stabilized components, e.g., non-geometrically stabilized internal particles; at least two, or three, or four, components chosen from the group of the particle matrix, the particle coating, the super matrix, and the outer coating (if present), provides a molecular weight cutoff that prevents molecules larger than about 150,000 daltons from coming into contact with the internal particle coating; the internal particle molecular weight cutoff is provided by a pore structure of the internal particle matrix, and that pore structure results, e.g., from cross-linking of the internal particle gel; the molecular weight cutoff the super matrix is provided by a pore structure of the super matrix.

Preferred embodiments lack an outer coating.

In preferred embodiments the outer surface of the double (or higher order) composite microreactor is a gel, e.g., an alginate gel. In more preferred embodiments the outer surface of the composite microreactor is a gel, e.g., an alginate gel, the outer surface of which has been modified, e.g., by cross-linking, to produce a covalently modified gel surface, e.g., to form a coating.

In preferred embodiments the internal particle coating is polylysine of about 5 kDa to less than about 15 kDa, or about 5 kDa to less than about 10 kDa, e.g., 9 kDa–10 kDa, and the particle coating is polylysine of about 5 kDa to less than about 15 kDa, or about 5 kDa to less than about 10 kDa, e.g., about 9 kDa–10 kDa. Also preferred are polyaminoacid, e.g., PLL or PLO, coatings in the range of 1 or 2–10 kD, preferably in the range of 1–2, 1–3, or 1–4 kD.

In preferred embodiments the internal particle coating is polylysine of about 1 kDa–4 kDa (or about 1 kDa-less than 4 kDa) e.g., about 2 kDa–3 kDa, and the particle coating is polylysine of about 5 kDa to less than about 15 kDa, or about 5 kDa to less than about 10 kDa, e.g., about 9 kDa–10 kDa. Also preferred are polyaminoacid, e.g., PLL or PLO, coatings in the range of 1 or 2–10 kD, preferably in the range of 1–2, 1–3, or 1–4 kD.

In preferred embodiments the internal particle coating is polylysine of about 1 kDa–4 kDa (or about 1 kDa-less than 4 kDa) e.g., about 2 kDa–3 kDa, and the particle coating is polylysine of about 1 kDa–4 kDa (or about1 kDa-less than 4 kDa) e.g., about 2 kDa–3 kDa. Also preferred are polyaminoacid, e.g., PLL or PLO, coatings in the range of 1 or 2–10 kD, preferably in the range of 1–2, 1–3, or 1–4 kD.

In preferred embodiments the outer component of the double composite microreactor, i.e., the component in contact with the recipient, is at least 50, 75, 90, 95, 97, or 98%, water.

In preferred embodiments one or more components of the double composite microreactor is of sufficient diameter, or of sufficient thickness, such that it imposes a substantial distance (or separation) between recipient cells, e.g., lymphocytes, macrophages, or NK cells, and the source of a therapeutic substance. In more preferred embodiments the thickness (e.g., the distance between its inner surface and its outer surface) of a component, e.g., a matrix, e.g., a particle matrix or super matrix, is: at least 5, 10, 20, 50, 75, 100, or 200 microns. In more preferred embodiments the distance between recipient cells and the source of a therapeutic substance is: at least 5, 10, 20, 50, 75, 100, or 200 microns; sufficient such that exposure of the source of a therapeutic substance to small molecules (e.g., molecules which are not excluded by a component which excludes IgG, e.g., cytokines, nitric oxide (NO), and other toxic moieties) released by recipient cells is substantially reduced (e.:g., by diffusion), e.g., reduced at least 10, 20, 50, 75, or 90%; sufficient such that the concentration of small molecules (e.g., molecules which are not excluded by the semipermeable barrier-components of the double composite microreactor, e.g., cytokines, NO, and other toxic moieties) released by recipient cells is substantially reduced (e.g., by diffusion), e.g., reduced at least 10, 20, 50, 75, or 90% at the source of a therapeutic substance. In more preferred embodiments: the distance is supplied by one or both of the particle matrix and the super matrix.

In preferred embodiments one or more components of the double composite microreactor is of sufficient diameter, or of sufficient thickness, such that it imposes a substantial distance (or separation) between recipient cells, e.g., lymphocytes, macrophages, or NK cells, and one or both of the source of a therapeutic substance or donor antigen (other than the therapeutic substance) released by the source (e.g., donor proteins, which could stimulate a recipient response against donor tissue). In more preferred embodiments the thickness (e.g., the distance between its inner surface and its outer surface) of a component, e.g., a matrix, e.g., a particle matrix or super matrix, is: at least 5, 10, 20, 50, 75, 100, or 200 microns. In more preferred embodiments the distance between recipient cells and the source of a therapeutic substance is: at least 5, 10, 20, 50, 75, 100, or 200 microns; sufficient such that the amount, number, or concentration of a donor antigen, released into the recipient, or contacting recipient cells, is substantially reduced (e.g., by diffusion, or by trapping in or exclusion by the component or components which supply the separation), e.g., reduced by at least 10, 20, 50, 75, or 90%; sufficient such that contact of cells of the recipient with donor antigens, e.g., proteins, which protrude from or extend through the internal particle matrix or internal particle coating, or both, is substantially reduced (e.g., by diffusion, or by trapping in or exclusion by the component or components which supply the separations, e.g., reduced by at least 10, 20, 50, 75, or 90%; sufficient to inhibit acute release of donor antigens. In more preferred embodiments: the distance or separation is supplied by one or both of the particle matrix and the super matrix.

As used herein, a source of a therapeutic substance can include a composition of matter which produces or releases a therapeutic substance, e.g., a protein, e.g., an enzyme, hormone, antibody, or cytokine, a sense or anti-sense nucleic acid, e.g., DNA or RNA, or other substance which can exert a desired effect on a recipient. The therapeutic substance can also be a composition of matter which absorbs or modifies or detoxifies a substance produced by the recipient. The source of a therapeutic substance can be a tissue or a living cell; a eukaryotic cell, e.g., a rodent, canine, porcine, or human cell; a prokaryotic cell, e.g., a bacterial cell; a fungal or plant cell; a cell which is genetically engineered, e.g., a cell which is genetically engineered to produce a protein, e.g., a human protein. The source of a therapeutic substance can be or include an autologous, an allogeneic, or a xenogeneic cell. For example, the cell is: an autologous cell, i.e., a cell which is taken from the individual recipient into which the cell will be implanted; an allogeneic cell, i.e., a cell which is taken from a different individual of the same species as the recipient into which the cell will be implanted; a xenogeneic cell, i.e., a cell which is from a different species than the recipient into which the cell will be implanted. In the case of an allogeneic cell, the cell can be fully matched or partially matched for MHC class I loci, fully matched or partially matched for MHC class II loci, and fully matched or partially matched for minor loci.

Embodiments of the invention feature the use of coatings, which, result in a decrease in the volume of the coated particle, as is described in PCT/US96/03135 and U.S. patent application Ser. No. 08/402,209, Filed Mar. 10, 1995.

The number of host molecules which can invade a component of a composite microreactor decreases substantially in the inward direction. As is discussed herein, the inner most member of a double composite microreactor is an internal particle. An internal particle is embedded in the next most outermost component, the particle matrix. The particle is in turn embedded in the next most outer component, the supermatrix. Of a population of molecules which invades the supermatrix only a small proportion will be able to enter a particle matrix, and only a small proportion of those that enter a particle matrix will be able to enter an internal particle. Thus, relatively small numbers of rescue agents, when placed in an inner component, can have a substantial effect in terms of inactivating host molecules which would otherwise have a deleterious effect on the implanted cells. As relatively few host molecules will reach the inner components, as compared with the outer most components, e.g., the super matrix, a given number of rescue agent molecules will be more efficacious and able to longer avoid saturation by host molecules if they are placed in a more inner component, e.g., the internal particle or even the particle of a double composite. If a comparable number of rescue agent molecules were presented at the surface of the device, they would be rapidly overwhelmed and thus inactivated by the relatively large number of host molecules. However, as each barrier, e.g., coating, or supermatrix or matrix, serially reduces the population of invading host molecules, a given number of rescue agent molecules are more efficacious in preserving function.

Composite Microreactors
Structural Components

FIG. 1 is a schematic diagram of a simple or single composite microreactor (10). The composite microreactor (10) contains at least one, and preferably a plurality of internal particles (20). An internal particle (20) includes one or a plurality of sources (30) of a therapeutic or otherwise desirable substance. The sources (30) are embedded carried on, adhered to, or in an internal particle matrix (40). The internal particle (20) can optionally include an internal particle coating (50). The internal particles can be embedded in a super matrix (60). The composite microreactor 10 can (optionally) include an outer coating (70).

The diameter of the composite microreactor (10) is preferably between 100 microns and 4 millimeters, between 300 and 1200 microns, between 300 and 1500 microns, between 400 and 1000 microns, or between 400 and 800 microns. More preferably the diameter is about 600 microns.

The diameter of the internal particles (20) before application of a volume-reducing coating (described below) is preferably between 50 and 700 microns, more preferably between 100 and 500 microns, more preferably between 200 and 400 microns, and most preferably about 300 microns in diameter. The diameter of the internal particles (20) after application of a volume-reducing coating (described below) is preferably between 35 and 500 microns, more preferably between 75 and 400 microns, more preferably between 100 and 300 microns, and most preferably about 200 microns in diameter.

As is discussed in more detail elsewhere herein, the source 30 can be a cell, or a group of cells, e.g., an islet. The sources of an internal particle can all be of one type or more than one type of source can be included in an internal particle. Furthermore, the composite microreactor 10 can include more than one type of internal particle (20), e.g. the composite microreactor 10 can include a first type of internal particle (20) having within it a first source, e.g., a first type of cell, and a second type of internal particle (20) having within it a second source, e.g., a second type of cell.

The internal particle matrix (40) can be a gel, e.g., a hydrogel, e.g., alginate or agarose. The internal particle matrix can also be a solid particle, e.g., a glass bead, or a porous structure, on which anchorage dependent cells can be seeded. The internal matrix (40) can have immunoisolative properties. In some embodiments it has little or no ability to exclude low molecular weight species, e.g., IgG or complement, with this property being relegated to other components of the composite microreactor (10). The internal particle matrix (40) can be rendered immunoisolating by controlling its porosity, e.g., such that it hinders the passage of molecules of relatively large molecular weight, or by adding to it components, e.g., polyethylene oxide (PEO), polystyrene sulfonic acid (PSA), or polyornithine (PLO) which hinder the passage of molecules of relatively large molecular weight. Regardless of the method of controlling its permeability, the internal matrix (40) will, in preferred embodiments will hinder the passage, and preferably, essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells. The internal matrix (40) need not be anti-fibrotic and need not be biocompatible. The composite microreactor (10) can include more than one type of internal particle (20), e.g., the composite microreactor (10) can include a first type of internal particle (20) having within it a first type of internal matrix (40) and a second type of internal particle (20) having within it a second type of internal matrix (40).

The internal particle coating (50) is optional. It can be made of a polyaminoacid, e.g., polylysine (PLL), PLO, chitosan, or PAN-PVC, or any coating used to coat noncomposite microreactors. In addition, the coating can be a formed by modifying the structure of the matrix, e.g., the matrix can be cross-linked, e.g., with metal ions, e.g., Ba or Fe ions, or by photo-cross-linking, to form an coating. A preferred coating is polylysine having a molecular weight of less than 15 kDa, more preferably of less than 10 kDa, more preferably of less than 5 kDa. Particularly preferred are polylysines with a molecular weight of about 3–4 kDa, e.g., 3.7 kDa, or about 9 kDa–10 kDa, e.g., 9.7 kDa. Preferred coatings are volume-reducing coatings. Furthermore, the composite microreactor 10 can include more than one type of internal particle (20), e.g., the composite microreactor 10 can include a first type of internal particle (20) having a first type of internal particle coating and a second type of internal particle (20) having a second type of internal particle coating (50). Because, in some embodiments, the internal particles coating (50) need not be biocompatible and need not be anti-fibrotic, other properties of the internal coating (50), e.g., its ability to immunoisolate, can be optimized without the necessity to allow confer biocompatibility or anti-fibrotic activity.

Super matrix (60) can be a gel, e.g., a hydrogel, e.g., alginate or agarose. The super matrix (60) can have immunoisolative properties. In some embodiments it can have little or no ability to exclude low molecular weight species, e.g., IgG or complement, with this property being relegated to other components of the composite microreactor (10). The super matrix (60) can be rendered immunoisolating by controlling its porosity, e.g., such that it hinders the passage of molecules of relatively large molecular weight or by adding to it components, e.g., PEO, PSA, or PLO which hinder the passage of relatively large molecules. Regardless of the method of controlling its permeability, the super matrix (60) will in preferred embodiments, will hinder the passage, and preferably essentially completely prevent the passage of: molecules having a molecular weight of more than about 50 kDa, preferably more than about 100 kDa, preferably more than about 150 kDa, and most preferably more than about 400 kDa; or of immune system components such as Ig molecules or complement; or recipient-derived cells. The super matrix (60) need not be anti-fibrotic and need not be biocompatible if a more proximal or more exterior component supplies these functions.

A rescue agent can be included in the internal particle matrix (40). However, the preferred location for a rescue agent is the super matrix (60). Positioning in the super matrix (60) allows inhibition of host molecules before they reach the internal particle (20).

Outer coating (70) is optional. It can be made of a polyaminoacid, e.g., PLL or PLO, chitosan, or PAN-PVC, or any coating used to coat non-composite microreactors. Alternatively, the coating can be formed by modifying the structure of the matrix, e.g., the matrix can be cross-linked, e.g., with metal ions, e.g., Ba or Fe ions, or by photo-cross-linking, to form an coating. A preferred coating is polylysine having a molecular weight of less than 15 kDa, more preferably of less than 10 kDa, more preferably of less than 5 kDa. Particularly preferred are polylysines with a molecular weight of about 3–4 kDa, e.g., 3.7 kDa, or about 9 kDa–10 kDa, e.g., 9.7 kDa. Preferred coatings are volume-reducing coatings. The outer coating (70) need not be immunoisolating if other components supply this function.

The multi-component structure of the composite microreactor allows selection of materials which can optimize performance. Coating materials which are highly immunoisolating, but less desirable in terms of their biocompatibility or anti-fibrotic activities, can be used in the internal particle coating. The multi-component structure also allows for multiple lines of defense against invasion by recipient immune system components. E.g., the use of an outer coating which passes 1 in $10^2$ recipient IgG molecules, a super matrix which passes 1 in $10^2$ recipient IgG molecules, and an internal particle coating which passes 1 in $10^2$ recipient IgG molecules, results in a composite pass rate of only about 1 in $10^6$.

The multicomponent structure of composite reactors also allow a rescue agent to be placed in a zone or compartment between the source of a therapeutic substance and the host.

The ability to segregate functions also allows construction of composite microreactors the life of which are roughly commensurate with the useful life of the enclosed sources. For example, gelatin, which weakens the matrix, could be added. If it is necessary to strengthen the matrix, fibers can be added.

A preferred composite microreactor is one in which: the composite microreactor contains at least two internal particles; the source of a therapeutic or otherwise desirable substance is a cell, e.g., an islet cell; the internal particle matrix is alginate; the internal particle includes an internal particle coating of polylysine; the internal particles are embedded in a super matrix of alginate; and the composite microreactor includes an outer coating of polylysine; the polylysine of the internal particle coating is of a molecular weight of between 2 and 10 kDa; the polylysine of the outer coating is of a molecular weight of between 2 and 10 kDa; the internal particles are geometrically stabilized, as is described below; the composite microreactor is generally stabilized, as is discussed in PCT/US96/03135 and U.S. patent application Ser. No. 08/402,209, Filed Mar. 10, 1995; the super matrix is free of fissures or other defects which arise form the use of internal particles which have not been geometrically stabilized; the diameter of an internal particle, is between 100 and 400 microns, preferably about 200 microns; the diameter of the composite microreactor is between 400 and 800 microns, preferably about 600 microns, and a rescue agent is incorporated into the super matrix.

As described above, the internal particle (20) can consist of sources embedded in a matrix, the matrix being enclosed in an internal particle coating. The internal particle (20) can also have other structures. For example, the inner particle can consist of a solid bead, e.g., a plastic bead, a sepharose bead, or a glass bead, on which cells, e.g., anchorage dependent cells, are allowed to grow. Cells can be allowed to grow on a surface of the solid bead or, if they are present, within interstitial spaces of the bead. Such an internal particle can be coated as described herein, or left uncoated. The internal particle can be coated or left uncoated. The internal particle, can be embedded in a supper matrix, the super matrix being enclosed by coating.

Composite microreactors can also contain fibers or materials to enhance the mechanical strength of the sphere. Similarly, the composite material can contain substances such as PEO which may act to repel protein and to hinder the fibrotic response. Other materials such as gelatin or collagen can also be added to either increase or decrease the porosity so as to influence the transport properties (permeability/and or molecular weight cutoff).

In addition to advantages, such as ease of retrieval, the embodiments of the invention permits the use of immunoprotectants which are not biocompatible. Materials which alone might be digested by enzymes, or which might trigger a fibrotic response when they come into direct contact with host tissues can be used to form permselective barriers. Methods of the inventor can also be used to alginate-coat particles made of neutral or positively-charged substances. More importantly, the alginate coating furnishes the composite structure with a physical barrier of substantial thickness versus the "coating" formed by mere electrostatic interactions. The composite structure (ranging in diameter from <50 µm to >5 mm) can be made of any material.

Internal particles can be of any shape, including, for example, planar, cubical, tubular, and disk-shaped particles and chambers, or other shapes which might otherwise become fibroencapsulated.

The ratios of the volume of the internal particles to the volume of the composite microreactor can be tailored to particular applications, but preferred ratios are 0.5:5.0, preferably 1.0:3.5, more preferably 1.0:2.5, or 1.0:3.0.

Higher Order Composites

Figure 2:
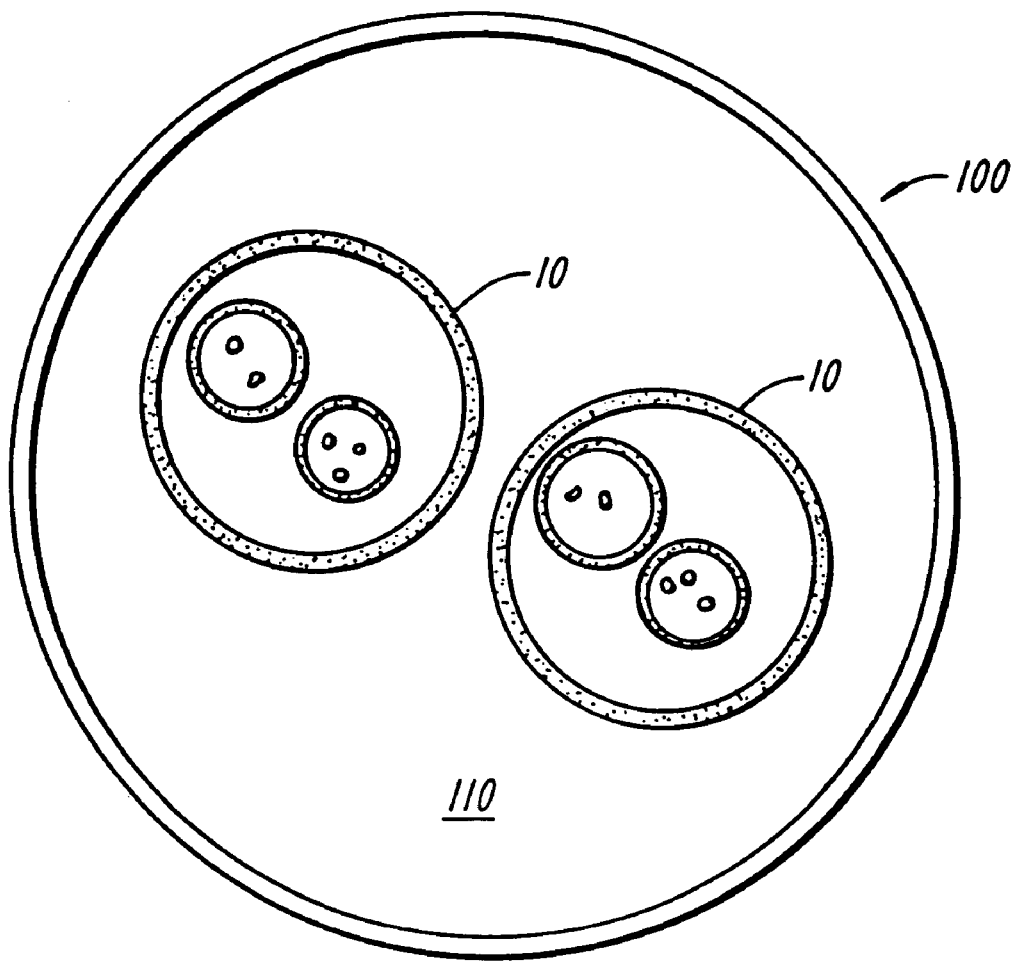
FIG. 2 is a schematic diagram of a double composite microreactor.

Embodiments of the invention include higher order composite microreactors, e.g., a double composite in which single composite microreactors (10) are embedded in a matrix which is (optionally) coated with an outer coating. Accordingly, FIG. 2, shows a second order, or double composite microreactor (100).

The double composite microreactor (100) contains one or a plurality of composite microreactors (10) (as described above and elsewhere herein) embedded in a double composite microreactor matrix or super matrix (110) which is (optionally) enclosed in a double composite microreactor outer coating (120).

The diameter of the double composite microreactor (100) is preferably between 100 microns and 4 millimeters, between 300 and 1500 microns, between 400 and 1000, or between 500 and 900 microns. More preferably the diameter is about 600–800 microns.

Double composite microreactor matrix or super matrix (110) can be a gel, e.g., a hydrogel, e.g., alginate or agarose. The double composite microreactor matrix or super matrix (110) can have immunoisolative properties. In some embodiments it can have little or no ability to exclude low molecular weight species, e.g., IgG or complement, with this property being relegated to other components of the composite microreactor (10). The double composite microreactor matrix or super matrix (110) can be rendered immunoisolating by controlling its porosity, e.g., such that it hinders the passage of molecules of relatively large molecular weight or by adding to it components, e.g., PEO, PSA, or PLO which hinder the passage of relatively large molecules. Regardless of the method of controlling its permeability, the matrix or super matrix (110) will, in preferred embodiments will hinder the passage, and preferably, essentially completely prevent the passage of molecules having a molecular weight of more than about 50 kDa, preferably more than about 100 kDa, preferably more than about 150 kDa, and most preferably more than about 400 kDa; or of immune system components such as Ig molecules or complement; or recipient-derived cells. The double composite microreactor matrix (110) need not be anti-fibrotic and need not be biocompatible if a more proximal or more exterior component supplies these functions. In double composite, the matrix of the inner most particle is usually referred to as the internal particle matrix. The matrix in which the internal particles are embedded is usually referred to as the particle matrix, and the matrix in which the single composite particles are embedded is usually referred to as the super matrix.

Double composite microreactor outer coating (120) is optional. It can be made of a polyaminoacid, e.g., PLL, PLO, chitosan, or PAN-PVC, or any coating used to coat non-composite microreactors. A preferred coating is a poly amino acid, e.g., polylysine, having a molecular weight of less than 15 kDa, more preferably of less than 10 kDa, more preferably of less than 5 kDa. Particularly preferred are polylysines with a molecular weight of about 3–4 kDa, e.g., 3.7 kDa, or about 9 kDa–10 kDa, e.g., 9.7 kDa. Preferred coatings are volume-reducing coatings. The double composite microreactor outer coating (120) need not be immunoisolating if other components supply this function.

Other embodiments of the invention include higher order composite microreactors, e.g., third order composites which include double composite microreactors embedded in a matrix and (optionally) enclosed in an outer coating, and forth order composites, which includes third order composites embedded in a matrix and (optionally) enclosed in an outer coating. The materials and methods discussed for use in simple and double composites can be used for the matrices and coatings of higher order composites.

The multicomponent structure of double (or higher order) composites also allows a rescue agent to be placed in a zone or compartment which is interposed between the source of a therapeutic substance and the host. E.g., a source of a therapeutic substance can be disposed within the internal particle and one or more rescue agents disposed in one or more of the particle matrix or the super matrix.

Formation of Composite Microreactors

Composite microreactors can be made by materials which are analogous with the methods used to make internal particles: individual or small numbers of internal particles (rather than cells) are embedded in a matrix (referred to herein as a super matrix to distinguish it from the internal particles matrix) and an (optional) outer coating applied.

For example, after the internal particles are prepared and, e.g., either coated or otherwise treated, e.g., cross-linked, they should be washed in medium to prevent the existing microparticles from sticking to each other (particles that have not been coated should be washed in calcium and magnesium free medium), mixed with a liquid hydrogel such as alginate, and formed into a composite microparticle with a diameter from less than 50 $\mu$m up to more than 5 mm. For example, in a method which is analogous to that described above for the creation of the internal particles, a mixture of internal particles in a liquid gel can be extruded through an 18 gauge catheter to form composite microreactors.

As is discussed elsewhere herein, it may be desirable to geometrically stabilize the internal particles before incorporating them into a composite microreactor.

The super matrix of a composite microreactor can provide a semipermeable shell of a hydrogel material around all of the encompassed internal particles can provide a physical barrier of substantial thickness compared to the individual coatings on each of the microcapsules. Electrostatic interactions in the super matrix can contribute to immunoisolation.

The super matrix can be made of the same material as the internal particle matrix or it can differ from the matrices of some or all of the internal particle matrices.

A composite microreactor can contain internal particles of any shape, including, for example, planar, cubical, tubular, and disk-shaped particles and chambers, which might otherwise become fibroencapsulated.

A composite microreactor can also contain other substances to modify the properties of the composite microreactor and can, e.g., include fibers or materials in addition to the hydrogel matrix and internal particles; to enhance the mechanical strength of the composite microreactor. Similarly, the composite microreactors and particularly the super matrix, can include substances such as PEO which act to repel proteins and to hinder the fibrotic response. Other materials such as gelatin or collagen can also be added to the super matrix to either increase or decrease the porosity so as to influence the transport properties (permeability and/or molecular weight cutoff) of the composite microreactors.

Higher order composites can be made by analogous methods.

Outer Coating

Composite microreactors can (optionally) be provided with an outer coating. Although any coating used with non-composite microreactors or for internal particles can be used for the outer coating, other coatings, or no coating, can be used as well. Because the various properties need by the implanted device, e.g., biocompatibility, the ability to resist fibrotic encapsulation, the ability to prevent recipient immune inactivation of the implanted donor tissue, can be distributed among the various components of the composite microreactor, the outer coating need not supply all of these properties. It may be desirable to geometrically stabilize the supermatrix prior to application of a coating.

Antibody Combinatorial Libraries and Engineered Binding Proteins

Monoclonal antibodies can also be generated by other methods well known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies (for descriptions of combinatorial antibody display see e.g., Sastry et al. 1989 *PNAS* 86:5728; Huse et al. 1989 *Science* 246:1275; and Orlandi et al. 1989 *PNAS* 86:3833).

Combinatorial libraries can be screened to obtain members of the library with a desired binding activity, and to identify the active species, by methods that have been described (see, e.g., Gordon et al., *J. Med. Chem., op. cit.*). These include affinity chromatography with an appropriate "receptor" to isolate ligands for the receptor, followed by identification of the isolated ligands by conventional techniques (e.g., mass spectrometry and NMR). Preferably, the soluble receptor is conjugated to a label (e.g., fluorophores, colorimetric enzymes, radioisotopes, or luminescent compounds) that can be detected to indicate ligand binding. Alternatively, immobilized compounds can be selectively released and allowed to diffuse through a membrane to interact with a receptor.

Combinatorial libraries of compounds can also be synthesized with "tags" to encode the identity of each member of the library (see, e.g., W. C. Still et al., International Application WO 94/08051). In general, this method features the use of inert but readily detectable tags, that are attached to the solid support or to the compounds. When an active compound is detected the identity of the compound is determined by identification of the unique accompanying tag. This tagging method permits the synthesis of large libraries of compounds which can be identified at very low levels among to total set of all compounds in the library.

Specific engineered binding proteins with high affinities for targets can be made according to methods known to those in the art. For example, proteins that bind specific DNA sequences may be engineered, and proteins that bind a variety of targets, especially protein targets (Ladner, R.C., et al., U.S. Pat. No. 5,233,409; Ladner, R.C., et al., U.S. Pat. No. 5,403,484) may be engineered and used in the present invention as the FcαR binding determinant or as the target binding determinant, as appropriate. Further, the methods of these libraries can be used in screens to obtain binding determinants that are mimetics of the structural determinants of antibodies.

In particular, the Fv binding surface of a particular antibody molecule interacts with its target ligand according to principles of protein-protein interactions, hence sequence data for $V_H$ and $V_L$ (the latter of which may be of the κ or λ chain type) is the basis for protein engineering techniques known to those with skill in the art. Details of the protein surface that comprises the binding determinants can be obtained from antibody sequence information, by a modeling procedure using previously determined three-dimensional structures from other antibodies obtained from NMR studies or crytallographic data. See for example Bajorath, J. and S. Sheriff, 1996, *Proteins: Struct., Funct., and Genet.* 24 (2), 152–157; Webster, D. M. and A. R. Rees, 1995, "Molecular modeling of antibody-combining sites," in S. Paul, Ed., *Methods in Molecular Biol.* 51, Antibody Engineering Protocols, Humana Press, Totowa, N.J., pp 17–49; and Johnson, G., Wu, T. T. and E. A. Kabat, 1995. "Seqhunt: A program to screen aligned nucleotide and amino acid sequences," in *Methods in Molecular Biol.*51, op. cit., pp 1–15.

Complement

Antibodies, naturally occurring or engineered binding ligands of elements of the classical or alternate complement pathways, or of molecules which activate these pathways are particularly preferred rescue agents.

The term "complement" refers to a set of more than 30 serum proteins that are universally present without prior exposure to a particular antigen (see, (Liszewski, M. et al., 1993, Fundamental Immunol., 3rd Ed., W. Paul Ed. Ch. 26 "The Complement System" p. 917). The function of the complement system is modification of the membrane of an infectious agent, and promotion of an inflammatory response through cell action. Complement proteins are converted to active forms by a series of proteolytic cleavages. Production of a reactive C3b protein can occur quickly and efficiently via the "classical" complement pathway, or slowly and inefficiently via the "alternative" pathway.

The alternative complement pathway differs further from the classical in that it functions independent of a specific antibody; it comprises as few as four protein components; and these components are of lower molecular weight than the largest proteins of the classical pathway. The four proteins of the alternative pathway are Factor B, Factor D, properdin, and C3, of $M_r$ 93 kDa, 25 kDa, 110–220 kDa, and 190 kDa, respectively. The concentrations in plasma in μg/ml are 225, 3, 25, and 1,200, respectively. The classical pathway includes a very high molecular weight protein, C1q, of $M_r$ 410 kDa. Complement is characterized also by tight regulation at several levels, to control potential destruction of healthy self tissue by the products of this series of proteolytic activities. For example, a plasma protein Factor H, $M_r$ 150 kDa (concentration 500 μg/ml in plasma) binds activated C3b and inhibits its activity. Tissues contain a cell-bound protein, CD55 or CDAF, with inhibitory activity for C3b, which plays a similar function as Factor H.

C3 is secreted by monocytes and macrophages; a complex of Factors B and D and properdin cleave C3 to yield the products C3a and C3b. These products promote mast cell degranulation, releasing inflammatory molecules such as histamine, proteases, lysozyme, acid hydrolases, and myeloperoxidase. Opsonization of target cell membranes promotes lysis and phagocytosis.

The alternative pathway is triggered by the presence of microbial surfaces or components, such as lipopolysaccharide.

Coupling Technologies for Cross-linking a Rescue Agent to an Implantable Device Component In many cases the immunoisolating properties of the implantable device, together with the size and other physical characteristics of the rescue agent will insure that the rescue agent is held within the implantable device. In some embodiments, though, it is desirable to link the rescue agent to another entity, to increase its size, to anchor it within the implantable device, to maintain it within a compartment of an implantable device or to otherwise inhibit its diffusion out of the device.

Rescue agents can be bound to carrier molecules, insoluble substrates, or to other components of an implantable device. Rescue agent ligands can be coupled to these entities by procedures known to one of ordinary skill in the art.

The term "coupling agent" as used herein, refers to a reagent capable of coupling or cross-linking a rescue agent to another component. e.g., to an implantable device component. Any bond which is capable of linking the components such that they are stable under physiological conditions for the time needed for administration and treatment is suitable, and covalent linkages are preferred. A coupling agent should function under conditions of temperature, pH, salt, solvent system, and other reactants that substantially retain the chemical stability of the rescue agent. Coupling is preferably performed prior to encapsulation of the biological material.

A coupling agent can link components without elements of the coupling agent remaining added to the final components of the implantable device. Another coupling agent can cause the addition of a molecular element of the coupling agent to the linked components. For example, a coupling agent can be a cross-linking agent that is a homo-or heterobifunctional molecule, wherein one or more atomic components of the agent can be retained in the composition. A coupling agent that is not a cross-linking agent can be removed entirely during the coupling reaction, so that the molecular product can be composed entirely of the rescue agent and the coupled component.

Many coupling agents react with an amine and a carboxylate, to form an amide, or an alcohol and a carboxylate to form an ester. Coupling agents are known in the art, see, e.g., M. Bodansky, "Principles of Peptide Synthesis", 2nd ed., referenced herein, and T. Greene and P. Wuts, "Protective Groups in Organic Synthesis," 2nd Ed, 1991, John Wiley, N.Y. Coupling agents should link component moieties stably such that there is only minimal or no denaturation or deactivation of the rescue agent, which in general can be more labile to conditions of temperature, pH, salt, and non aqueous solvent, than is the more stable implantable device component.

A variety of coupling agents, including cross-linking agents, can be used for covalent conjugation. Examples of cross-linking agents include N,N'-dicyclohexylcarbodiimide (DCC; Pierce), N-succinimidyl-S-acetyl-thioacetate (SATA), N-succinimidyl-3-(2-pyridyldithio)propionate (SPDP), ortho-phenylenedimaleimide (o-PMD), and sulfosuccinimidyl 4-(N-maleimidomethyl) cyclohexane-1-carboxylate (sulfo-SMCC). See, e.g., Karpovsky et al. *J Exp. Med.* 160:1686, 1984; and Liu, MA et al., *Proc. Natl. Acad. Sci. USA* 82:8648, 1985. Other methods include those described by Paulus, *Behring Ins. Mitt.*, No. 78, 118–132, 1985; Brennan et al. *Science* 229:81–83, 1985, and Glennie et al., *J. Immunol.*, 139: 2367–2375, 1987. A large number of coupling agents for peptides and proteins, along with buffers, solvents, and methods of use, are described in the Pierce Chemical Co. catalog, pages T-155-T-200, 1994 (3747 N. Meridian Rd., Rockford Ill., 61105, U.S.A.; Pierce Europe B. V., P.O. Box 1512, 3260 BA Oud Beijerland, The Netherlands), which catalog is hereby incorporated by reference.

DCC is a useful coupling agent (Pierce #20320; Rockland, Ill.). It promotes coupling of the alcohol NHS to another entity in DMSO (Pierce #20684), forming an activated ester which can be cross-linked to polylysine. DCC (N,N'-dicyclohexylcarbodiimide) is a carboxy-reactive cross-linker commonly used as a coupling agent in peptide synthesis, and has a molecular weight of 206.32. Another useful cross-linking agent is SPDP (Pierce #21557), a heterobifunctional cross-linker for use with primary amines and sulfhydryl groups. SPDP has a molecular weight of 312.4, a spacer arm length of 6.8 angstroms, is reactive to NHS-esters and pyridyldithio groups, and produces cleavable cross-linking such that, upon further reaction, the agent is eliminated so the rescue agent can be linked directly to the microcapsular component. Other useful conjugating agents are SATA (Pierce #26102) for introduction of blocked SH groups for two-step cross-linking, which is deblocked with hydroxylamine-HCl (Pierce #26103), and sulfo-SMCC (Pierce #22322), reactive towards amines and sulfhydryls. Other cross-linking and coupling agents are also available from Pierce Chemical Co. (Rockford, Ill.). Additional compounds and processes, particularly those involving a Schiff base as an intermediate, for conjugation of proteins to other proteins or to other compositions, for example to small molecules, for example, such as lazaroids or chelators, are disclosed in EPO 243,929 A2 (published Nov. 4, 1987).

Peptides and other agents which contain carboxyl groups can be joined to lysine ε-amino groups in one of the implantable device coatings either by preformed reactive esters (such as N-hydroxy succinimide ester) or esters conjugated in situ by a carbodiimide-mediated reaction. The same applies to rescue agents which contain sulfonic acid groups, which can be transformed to sulfonyl chlorides which react with amino groups. Rescue agents which have carboxyl groups can be joined to amino groups on a polypeptide by an in situ carbodiimide method. Rescue agents can also be attached to hydroxyl groups, of serine or threonine residues or to sulfhydryl groups, of serine or threonine residues or to sulfhydryl groups of cysteine residues.

Methods of the invention reduce or eliminate the need for immunosuppression in a recipient subject. In some instances, limited administration of immunosuppressive agents can be desirable. Immunosuppressive treatment can include: administering to the recipient adjunctive immunosuppression for less than one year, 180 days, 90 days, 60 days, or 30 days; administering a drug to the host animal at a dosage effective to inhibit fibrosis and inflammation around the uncoated particle, but at a dosage lower than that required to achieve the same effect when a rescue agent is not used. For example, cyclosporin A can be administered at a dosage that achieves a whole blood trough level of less than about 100 ng/ml in the host animal.

The invention is further illustrated by the following examples, which should not be construed as further limiting. The contents of all references, pending patent applications and published patents, cited throughout this application, are hereby expressly incorporated by reference.

See, "Short Protocols in Molecular Biology", Ed. F. Ausubel, 3rd Ed., 1995, Wiley, for the use of cyanogen bromide (CNBr)-activated Sepharose. CNBr pre-activated beads are available (Pharmacia Biotech, Piscataway, N.J.). Anti-IgG serum fractions can be obtained commercially also (Zymed Laboratories, South San Francisco, Calif.).

Implantation

Implantable devices can be implanted by methods known to those skilled in the art. The implantable devices can be implanted into a host by injection with a standard catheter or syringe, e.g., with a 16 gauge needle for beads less than 1000 μm in diameter. Larger implantable devices can be inserted via a small incision, e.g., with a catheter or funnel-like device. The beads are preferably implanted into the host intraperitoneally. The beads can also be implanted intramuscularly or subcutaneously. Alternatively, the beads can also be implanted into immunoprivileged sites such as the brain, testes, or thymus, where the host's immune response is least vigorous, as described in Chapter 7 of Lanza et al. (eds.), *Immunomodulation of Pancreatic Islets* (RG Landes, Texas, 1994). Composite implantable devices can also be introduced at a site where the substance provided by the composite implantable device is needed locally. E.g., a implantable device which provides α-interferon could be implanted in tumors. The implantable devices of the invention can be delivered to a subcutaneous site. The composite implantable devices can be inserted through a small surgically created opening using a gun/trocar type device that slips the beads under the skin.

A suitable host for the invention can be a subject or a patient. The term "subject," as used herein, refers to a living animal or human in need of therapy for, or susceptible to, a condition, which is remediable through implantable device implantation and reduction of potential host immune rejection of the implantable device. In preferred embodiments, the subject is a mammal, including humans and non-human mammals such as dogs, cats, pigs, cows, sheep, goats, horses, rats, and mice. In the most preferred embodiment, the subject is a human. The term "subject" does not preclude individuals that are normal in all respects. The subject can be a candidate for future treatment by microcapsular implantation, formerly have been treated surgically or by chemotherapy, and can be under treatment by microcapsular implantation, and can have been so treated in the past.

The term "patient," as used herein, refers to a human subject who has presented at a clinical setting with a particular symptom or symptoms suggesting treatment by implantation of implantable devices and suppression of the immune response concomitant to or subsequent to implantation. A patient's diagnosis can alter during the course of disease progression, such as development of further disease symptoms, or remission of the disease, either spontaneously or during the course of a therapeutic regimen or treatment.

EXAMPLES

Example 1
Retention of Antibody Molecules in an Alginate Implantable Device

Alginate (Pronova LVG sodium alginate, Protan, Drammen, Norway) implantable devices, 600 µm diameter, were produced and an implantable device sample was incubated for 90 min at room temperature in a solution of guinea pig antibody to pig insulin (Sigma Immunochemicals, St. Louis, Mo.). Poly-L-lysine (PLL; Sigma) of molecular weight 3.9 kD at 0.2% concentration was used to coat the microreactors, followed by 0.15% UP alginate, then by another layer of 0.2% PLL. At 3 days after formation and antibody inclusion, implantable devices with anti-pig insulin antibody, and control implantable devices lacking antibody, were incubated with $^{125}$I-insulin (NEN Radiochemicals, Billerica, Mass.) for 2h, washed several times, and radioactivity of samples where determined in a Cobra 5010 Packard counter.

Data in Table 1 show that over 96% of initial radioactivity in antibody-containing implantable devices is retained on day 2, 95% is retained on day 3, and 94% on day 5.

The decline in radioactivity, uncompensated for $^{125}$I decay with a 60d half-life, can reflect several dynamic biochemical processes: leakage of antibody from the implantable device; dissociation of antigen from antibody at the characteristic rate of the affinity constant; and denaturation of the antibody. The data show clearly that microencapsulated antibody molecules are retained to a statistically significant extent.

TABLE 1

Retention of labeled insulin by anti-insulin antibody-bearing implantable devices.

| Time (days) after insulin exposure | Coated reactor with antibody insulin | Coated control | Uncoated control |
|---|---|---|---|
| 1 | 9443 (100%) | 75 | 70 |
| 2 | 9115 (96%) | 0 | 0 |
| 3 | 9004 (95%) | 0 | 0 |
| 4 | 8877 (94%) | 0 | 0 |

Example 2
Single Composite Microreactors With Rescue Agents Disposed in the Internal Particle 1. 600 µm alginate beads (internal particle cores) containing porcine islets and anti-host IgG coupled to latex beads were produced. The latex-antibody beads are included in the internal core at a 1:500 volume/volume ratio of beads-to-alginate. The beads were 0.60 µm latex (polystyrene) microspheres (Bangs Laboratories, Inc., Fishers, Ind.). Affinity purified rabbit anti-dog IgG and the IgG fraction of rabbit anti-dog IgG (Rockland, Gilbertsville, Pa.) were coupled to the surface of the microspheres by protein absorption (maximized at the isoelectric point of the IgG) and covalent coupling to the carboxylate modified microspheres via activated COOH/activated NH2 binding.

2. The inner cores were coated with a layer of polylysine, a thin layer of alginate, and another layer of polylysine (0.2% 3.9K polylysine/0.15%alginate/0.2% 9K polylysine.

3. Coated internal particles were incorporated into an alginate matrix to provide a single composite microreactor about 900 µm in diameter.

Example 3
Single Composite Microreactors With Rescue Agents Disposed in the Internal Particle 1. 600 µm alginate beads (internal particle cores) containing porcine islets and anti-host IgM coupled to latex beads were produced. The latex-antibody beads were included in the internal particle core at a 1:500 volume/volume ratio of beads-to-alginate. The beads were 2.60 µm diameter latex (polystyrene) microspheres (Bangs Laboratories, Inc., Fishers, Ind.). The IgG fraction of rabbit anti-dog IgM µ (mµ chain specific) (Rockland, Gilbertsville, Pa.) was coupled to the beads by protein absorption (maximized at the isoelectric point of the Ig) and covalent coupling to the carboxylate modified microspheres via activated COOH/activated NH2 binding.

2. The inner cores were coated with a layer of polylysine, a thin layer of alginate, and another layer of polylysine (0.2% 3.9K polylysine/0.15%alginate/0.2% 9K polylysine.

3. Coated internal particles were incorporated into an alginate super matrix to provide a single composite microreactor about 900 µm in diameter.

Example 4
Double Composite Microreactors With Rescue Agents Disposed in the Internal Particle and In the Matrix 1. 600 µm alginate beads (internal particle cores) containing porcine islets and anti-host IgG coupled to latex beads were produced. The latex-antibody beads were included in the internal core at a 1:1,000 volume/volume ratio of beads-to-alginate. The beads were 0.60 µm latex microspheres (Bangs Laboratories, Inc., Fishers, Ind.).

Affinity purified rabbit anti-dog IgG and the IgG fraction of rabbit anti-dog IgG (Rockland, Gilbertsville, Pa.) were coupled to the beads by protein absorption (maximized at the isoelectric point of the Ig) and covalent coupling to the carboxylate modified microspheres via activated COOH/ activated NH2 binding.

2. The inner cores were coated with a layer of polylysine, a thin layer of alginate, and another layer of polylysine (0.2% 3.9K polylysine/0.15%alginate/0.2% 9K polylysine.

3. These coated internal particles were encapsulated to make single composite microreactors of about 900 μm in diameter. The alginate matrix (in which the internal particles are encapsulated) contained 0.60 μm latex microspheres (1:500 volume/volume ratio of beads-to-alginate) (Bangs Laboratories, Inc., Fishers, Ind.). These microspheres were conjugated with affinity purified rabbit anti-dog IgG and the IgG fraction of rabbit anti-dog IgG (Rockland, Gilbertsville, Pa.).

4. The single composite microreactors from step 3 were coated with 0.2% 9K polylysine to form particles.

5. The coated particles were encapsulated in an alginate supermatrix to form double composite microreactors of about 1200–1500 μm in diameter.

Example 5
Double Composite Microreactors With Multiple Rescue Agents Disposed in the Internal Particle and In the Matrix 1. 600 μm alginate beads (internal particle cores) containing porcine islets and rescue agents IgG coupled to latex beads were produced. Goat anti-dog C3 (ImmunoVision, Springdale, Ark.) and polyclonal goat anti-human C1q (CalBiochem, La Jolla, Calif.) (antibodies to human C1q cross react with other species) were coupled to the latex microspheres. The rescue-agent coupled latex beads were included in the internal core at a 1:1,000 volume/volume ratio of beads-to-alginate. The beads were 0.60 μm latex microspheres (Bangs Laboratories, Inc., Fishers, Ind.).

2. The inner cores were coated with a layer of polylysine, a thin layer of alginate, and another layer of polylysine (0.2% 3.9K polylysine/0.15%alginate/0.2% 9K polylysine.

3. The coated internal particles were incorporated into an alginate matrix to provide single composite microreactors about 900 μm in diameter. The alginate matrix (in which the internal particles were encapsulated) contained 0.60 μm latex microspheres (1:500 volume/volume ratio of beads-to-alginate) (Bangs Laboratories, Inc., Fishers, Ind.). Goat anti-dog C3 (ImmunoVision, Springdale, Ark.) and polyclonal goat anti-human C1q (CalBiochem, La Jolla, Calif.) (antibodies to human C1q cross react with other species) were coupled to the latex microspheres.

4. The single composite microreactors from step 3 were coated with 0.2% 9K polylysine to form particles.

5. The coated particles were encapsulated in an alginate supermatrix to form double composite microreactors of about 1200–1500 μm in diameter.

Example 6
Implantation of Microreactors Which Include Rescue Agents Into Dogs

The Microreactors of the Examples can be are introduced into dogs to test their efficacy. Microreactors of a single type, that is, from a single Example listed above can be introduced into a dog. Alternatively, more than one type of microreactor can be introduced into a single dog. For example, microreactors of Examples 2, 3, and 4 can be introduced into a single dog, and if desired distinguished by the size of the microreactor as well as by the size of the internal components. In other words, the size of the latex beads, which are available in a number of diameters, can be used to tag or identify a particular species of microreactor.

Briefly, dog experiments were performed as follows: before implantation the microcapsules were washed in serum free media 4 times with 10× volume and transported to Charles River PharmServices, Southbridge, Mass. Adult mongrel male dogs weighting 20–25 kilograms were used as recipients. Laparotomy was performed through a short 1–2 cm midline abdominal incision. 5–10 ml of microreactors (containing 3–5 c×10 4 porcine islets in total) were suspended in 75 ml of Hanks M199 media and distributed randomly into the peritoneal cavity by catheter. After implantation, the abdominal wall muscles and the skin wound were sutured closed.

The microspheres are left in the dogs for about 5–14 days then recovered and the viability of the islet ascertained. Control microreactors were also administered which were similar but did not include rescue agent -latex beads. The dogs received antibiotics and Aleve (naproxen, a nonprescription non-steroidal anti inflammatory). The dogs received no immunosuppressants.

Example 7
Single Composite Microreactors With Rescue Agents Disposed in the Internal Particle 1. 600 μm alginate beads (internal particle cores) containing porcine islets and anti-IL-1β and/or anti-TNFα coupled to latex beads are produced. The latex-antibody beads are included in the internal core at a 1:500 volume/volume ratio of beads-to-alginate. The beads are 0.60 μm latex (polystyrene) microspheres (Bangs Laboratories, Inc., Fishers, Ind.). Rabbit anti-human IL-1β and/or rabbit anti-human TNFα antibodies (Research Diagnostics, Flanders, N.J.) are coupled to the surface of the microspheres by protein absorption (maximized at the isoelectric point of the Ig) and covalent coupling to the carboxylate modified microspheres via activated COOH/activated NH2 binding. (The anti-human antibodies cross react with canine anti-IL-1β and anti-TNFα.)

2. The inner cores are coated with a layer of polylysine, a thin layer of alginate, and another layer of polylysine (0.2% 3.9K polylysine/0.15%alginate/0.2% 9K polylysine.

3. Coated internal particles are incorporated into an alginate matrix to provide a single composite microreactor about 900 μm in diameter.

Example 8
Double Composite Microreactors With Rescue Agents Disposed in the Internal Particle and In the Matrix 1. 600 μm alginate beads (internal particle cores) containing porcine islets and anti-IL-1β and/or anti-TNFα coupled to latex beads are produced. The latex-antibody beads are included in the internal core at a 1:1,000 volume/ volume ratio of beads-to-alginate. The beads were 60 μm latex microspheres (Bangs Laboratories, Inc., Fishers, Ind.). Rabbit anti-human IL-1β and/or rabbit anti-human TNFα antibodies (Research Diagnostics, Flanders, N.J.) are coupled to the surface of the microspheres by protein absorption (maximized at the isoelectric point of the Ig) and covalent coupling to the carboxylate modified microspheres via activated COOH/activated NH2 binding.

2. The inner cores are coated with a layer of polylysine, a thin layer of alginate, and another layer of polylysine (0.2% 3.9K polylysine/0.15%alginate/0.2% 9K polylysine.

3. These coated internal particles are encapsulated to make single composite microreactors of about 900 μm in diameter. The alginate matrix (in which the internal particles are encapsulated) contained 0.60 μm latex microspheres (1:500 volume/volume ratio of beads-to-alginate) (Bangs Laboratories, Inc., Fishers, Ind.). These microspheres are conjugated with rabbit anti-human IL-1β and/or rabbit anti-human TNFα antibodies (Research Diagnostics, Flanders, N.J.

4. The single composite microreactors from step 3 are coated with 0.2% 9K polylysine to form particles.

5. The coated particles are encapsulated in an alginate supermatrix to form double composite microreactors of about 1200–1500 μm in diameter.

Example 9
Double Composite Microreactors With Multiple Rescue Agents Disposed in the Internal Particle and In the Matrix 1. 600 μm alginate beads (internal particle cores) containing porcine islets and rescue agents IgG coupled to latex beads are produced. Goat anti-dog C3 (ImmunoVision, Springdale, Ark.) and polyclonal goat anti-human C1q (CalBiochem, La Jolla, Calif.) (antibodies to human C1q cross react with other species) were coupled to the latex microspheres. The rescue-agent coupled latex beads are included in the internal core at a 1:1,000 volume/volume ratio of beads-to-alginate. The beads are 0.60 μm latex microspheres (Bangs Laboratories, Inc., Fishers, Ind.).

2. The inner cores are coated with a layer of polylysine, a thin layer of alginate, and another layer of polylysine (0.2% 3.9K polylysine/0.15%alginate/0.2% 9K polylysine.

3. The coated internal particles are incorporated into an alginate matrix to provide single composite microreactors about 900 μm in diameter. The alginate matrix (in which the internal particles were encapsulated) contain 0.60 μm latex microspheres (1:500 volume/volume ratio of beads-to-alginate) (Bangs Laboratories, Inc., Fishers, Ind.). Rabbit anti-human IL-1β and/or rabbit anti-human TNFα antibodies (Research Diagnostics, Flanders, N.J.) are coupled to the latex beads.

4. The single composite microreactors from step 3 are coated with 0.2% 9K polylysine to form particles.

5. The coated particles are encapsulated in an alginate supermatrix to form double composite microreactors of about 1200–1500 μm in diameter.

Other Embodiments

Rescue agent-related methods of the invention can be used to treat a variety of disorders. These include disorders that result from the defective or insufficient production of a particular substance, e.g., enzyme or hormone, and other disorders, e.g., trauma-related disorders, such as spinal cord injury.

A number of well-characterized disorders caused by the loss or malfunction of specific cells in the body are amenable to implantable device-medicated replacement therapy. For example, in addition to the islets of Langerhans, which can be used for the treatment of diabetes as described above, hepatocytes can be used for the treatment of hepatic failure, adrenal gland cells can be used for the treatment of Parkinson's disease, nerve growth factor (NGF)-producing cells can be used for the treatment of Alzheimer's disease, factors VIII- and IX-producing cells can be used for the treatment of hemophilia, and endocrine cells can be used for the treatment of disorders resulting from hormone deficiency, e.g., hypoparathyroidism.

Moreover, by using recombinant DNA methods to supply a cell which produces a disease product, or encapsulating other tissues, implantable devices can be used to treat patients suffering from chronic pain, cancer (e.g., hairy cell leukemia, melanoma, and renal carcinoma), AIDS (treated by immunological augmentation), Kaposi's Sarcoma (treated by administration of interferon, IL-2, or TNF-α), primary hematologic disorders, patients with long-lasting aplasia, and patients who are myelosuppressed (treated by bone marrow transplantation and aggressive chemotherapy). Implantable devices should also be useful in the treatment of affective disorders, e.g., Huntington's Disease, Duchenne's Muscular Dystrophy, epilepsy, infertility. Implantable devices can also be used to promote wound healing and to treat traumatic, mechanical, chemical, or thermal injuries, e.g., spinal cord injuries, and in wound healing.

Implantation of specific cells can also serve to detoxify, modify, or remove substances from the circulation, e.g., drugs, poisons, or toxins. For example, the implantation of appropriate living cells restores normal physiologic function by providing replacement for the diseased cells, tissues, or organs, e.g., in hepatic encephalopathy (produced by liver disease) or uremia (produced by kidney failure).

In embodiments of the invention, the encapsulated cells can release fairly large molecules, e.g., IgG molecules. In many applications the critical host component which must be excluded is C1q, which has a molecular weight of about 410 kDa. Thus, the molecular weight cutoff will be about 410 kDa and molecules of up to this size can be released. Genetically engineered cells can also be used in the methods of the invention. For example, cells can be engineered to release larger products, e.g., IgG.

In each application, a sufficient number of composite implantable devices, containing the desired living cells, can be implanted into the patient, e.g., surgically or with a syringe. The implantable devices are implanted, e.g., intraperitoneally, for a systemic effect, or into a particular location, e.g., the brain to treat Parkinson's disease., or the spinal cord to chronic pain or treat spinal cord injuries, for a local effect.

The dose of implantable devices to be used is determined initially from results of in vitro studies. In addition, in vivo results in, e.g., mice, rats, or dogs will facilitate more accurate assessment of required doses, as these tests are generally predictive of efficacy in human patients. For example, canine insulin dependent diabetes represents an excellent model of cellular and humoral autoimmunity (Nelson, *Diabetes Spectrum* 5:324–371 (1992))

The implantable devices are intended to remain in the patient with viable donor cells for extended periods of time up to several months or years. However, if it is determined that the donor cells are no longer viable, e.g., by monitoring the patient's blood for a certain level of the protein secreted by the donor cells, it is a simple task to remove the implantable devices and renew the supply of beads in the patient.

Diabetes Mellitus

To treat diabetes, e.g., in a dog or human patient, the implantable beads preferably encapsulate isolated canine or porcine islets or other cells that produce insulin or insulin-like growth factor 1 (IGF- 1). Islets are prepared and encapsulated using procedures described above. Insulin secretory activity of the encapsulated cells or islets is determined both in static culture, e.g., expressed per islet volume, and based on the capability of the islets to respond to graded concentrations of glucose. These values are established as described above. Once the insulin secretion activity of a particular batch of encapsulated islets is determined, the proper number of beads can be determined and implanted into a diabetic patient. For example, to treat a human patient that requires 20 to 50 units of insulin per day, the total number of beads should be selected to contain a total of about 1.0 to 2.5 million porcine islets. For beads designed to contain, on average, 30,000 islets/ml of gel, the proper dosage would be beads made from 30 to 85 ml of gel.

Hemophilia

Hemophilia is an X-linked hereditary bleeding disorder caused by Factor VIII or Factor IX deficiency. Recombinant methods have now been successfully used to create Factor VIII- and Factor IX-producing cells as described above. Encapsulation in implantable devices and implantation of such cells according to the present invention can thus be used for an improved treatment for hemophilia.

Hepatic Diseases

Hepatocyte transplantation is useful not only for irreversible hepatic failure, but for several disease processes including hereditary enzyme abnormalities, acute hepatic failure, where the ability of the liver to regenerate can occur, and as a bridge to whole liver transplantation in patients who develop sudden hepatic failure, either because of medical progression or because of rejection-related complications.

Wong and Chang, *Biomat. Art. Cells Art. Org.,* 16:731 (1988), have demonstrated the viability and regeneration of microencapsulated rat hepatocytes implanted into mice. Viable hepatocytes were microencapsulated in alginate-poly-(L-lysine) and implanted intraperitoneally into normal and galactosamine-induced liver failure mice. Eight days after implantation in the mice with induced liver failure, the viability of the encapsulated rat hepatocytes increased from 42% to nearly 100%. After 29 days, the viability of the encapsulated hepatocytes implanted in normal mice also increased from 42% to nearly 100%. By contrast, free rat hepatocytes implanted into mice all died within four or five days after xenotransplantation. Implantable devices are well-suited to treat hepatic failure.

Other investigators have shown that microencapsulated hepatocytes continue the synthesis and secretion of many specific proteins and enzymes. Cai et al., *Hepatology,* 10:855 (1989), developed and evaluated a system of microencapsulation of primary rat hepatocytes. Urea formation, prothrombin and cholinesterase activity, the incorporation of tritiated leucine into intracellular proteins, and the immunolocation of synthesized albumin were monitored in culture. Despite gradual decreases in some of these activities, the encapsulated hepatocytes continued to function throughout the 35-day observation period. In addition, Bruni and Chang, *Biomat. Art. Cells Art. Org.,* 17:403 (1989),demonstrated the use of microencapsulated hepatocytes to lower bilirubin levels in hyperbilirubinemia. Microencapsulated hepatocytes were injected into the peritoneal cavity of Grunn rats. Bilirubin dropped from 14 milligrams/100 ml to 6 milligrams/100 ml, and remained depressed after 90 days. Again, implantable devices can be used as described above to treat these hepatic diseases.

Parkinson's Disease

Parkinson's disease is a neuronal system disease, involving a degeneration of the nigrostriatal dopaminergic system. Experimental work in both rodents and nonhuman primates has shown that transplantation of fetal tissue containing substantia nigra (dopaminergic) neurons from ventral mesencephalon to dopamine-depleted striatum reinstates near-normal dopamine interinnervation and reduces motor abnormalities. In addition, implantation of adrenal chromaffin cells has been shown to reverse chemically-induced Parkinson's disease in rodents.

Widner et al., *Transplant. Proc.,* 23:793 (1991), reported evidence of fetal nigral allograft survival and function up to 10 months after transplantation and immunosuppression (cyclosporin, azathioprine, and prednisone) in a human Parkinsonl's patient. Beginning from the second month after the transplantation, they observed a progressive decrease in limb rigidity, increased movement speed in a number of arm, hand, and foot movements, and prolonged "on" periods (greater than 80% increase) after a single dose of L-dopa.

Thus, transplantation of fetal neural tissue, or cells genetically engineered to produce dopamine and nerve growth factors or other neurotropic factors, should have a great potential as a new therapeutic approach in patients with neurological disorders. However, in the case of transplanted xenogeneic donor tissue, rejection would pose a serious problem, even by the combined approach of using an immunoprivileged site and by employing immunosuppressive drugs. Therefore methods of the invention permit a novel approach to this problem, i.e., the delivery of dopamine for the treatment of Parkinson's disease using encapsulated donor tissue harvested from animals or genetically engineered cells.

Alzheimer's Disease

An estimated 2.5 to 3.0 million Americans are afflicted with Alzheimer's disease. The disease is characterized by a progressive loss of cognitive function associated with degeneration of basal forebrain cholinergic neurons. Studies in animals indicate that Nerve Growth Factor (NGF), e.g., brain-derived neurotrophic factor (BDNF) and neurotrophin-3 (NT-3), available from Regeneron and Amgen, respectively, and other neurotropic factors normally act to support the viability and function of these neuron cells, and that continuous infusion of NGF into the ventricles can prevent injury-induced degeneration of cholinergic neurons as described in Williams et al., *P.N.A.S., USA,* 83:9231 (1986). This treatment correlates with improved cognitive function in rodents with memory impairment as described in Fisher et al., *Neurobiol. Aging,* 10:89 (1989).

These studies suggest that implantable devices containing grafts of recombinant or natural NGF-secreting tissue such as astroglial cells or developing skin, can be used to treat patients suffering from Alzheimer's disease.

Gene Therapy

Gene therapy is an approach to treating a broad range of diseases by delivering therapeutic genes directly into the human body. Diseases that can potentially be cured by gene therapy include diseases associated with the aging population such as cancer, heart disease, Alzheimer's disease, high blood pressure, atherosclerosis and arthritis; viral infectious diseases such as acquired immune deficiency syndrome (AIDS) and herpes; and inherited diseases such as diabetes, hemophilia, cystic fibrosis, and muscular dystrophy.

In one particular example, a favored approach for human gene therapy involves the transplantation of genetically-altered cells into patients, e.g., as described Rosenberg, et al., *New Eng. J Med.,* 323:570–578 (1988). This approach requires the surgical removal of cells from each patient to isolate target cells from nontarget cells. Genes are introduced into these cells via viral vectors or other means, followed by transplantation of the genetically-altered cells back into the patient. Although this approach is useful for purposes such as enzyme replacement therapy (for example, for transplantation into a patient of cells that secrete a hormone that diseased cells can no longer secrete), transplantation strategies are less likely to be suitable for treating diseases such as cystic fibrosis or cancer, where the diseased cells themselves must be corrected. Other problems commonly encountered with this approach include technical problems, including inefficient transduction of stem cells, low expression of the transgene, and growth of cells in tissue culture which can select for cells that are predisposed to cancer.

The methods of the invention are well suited to avoid these problems, because they allow the use of standard human cell lines of, e.g. fibroblast cells, epithelial cells such as HeLa cells, and hepatoma cells such as HepG2, as the implanted cells, rather than requiring the surgical removal of cells from the patient. These cell lines are genetically altered as required by standard techniques and are encapsulated and implanted into the patient. These cell lines are much easier to obtain, culture, and work with than individual patients' cells. Moreover, since the implantable devices prevent the patient's immune system from recognizing and attacking the implanted cells, any human cell lines can be used, making the technique of gene therapy more universally applicable.

Hypoparathyroidism

Acute and chronic symptoms of hypoparathyroidism result from untreated hypocalcemia, and are shared by both hereditary and acquired hypoparathyroidism. The hereditary form typically occurs as an isolated entity without other endocrine or dermatologic manifestations or, more typically, in association with other abnormalities such as defective development of the thymus or failure of other endocrine organs such as the thyroid or ovary. Acquired hypoparathyroidism is usually the result of inadvertent surgical removal of all the parathyroid glands, and is a problem in patients undergoing operations secondary to parathyroid adenoma or hyperplasia. Hypoparathyroidism has been treated in hypocalcemic rats by the administration of microencapsulated parathyroid cells that served as a bioartificial parathyroid. Parathyroid cells can also be encapsulated in implantable devices and used with the methods described herein in administration to animals and human patients.

Osteoporosis

The term osteoporosis covers diseases of diverse etiology that cause a reduction in the mass of bone per unit volume. These diseases can be treated by the administration of implantable devices containing cells that secrete insulin-like growth factor (IGF-1), estrogen in postmenopausal woman to reduce the negative calcium balance and decrease urinary hydroxyproline, androgens in the treatment of osteoporotic men with gonadal deficiency, or calcitonin for use in established osteolporosis.

Reproductive Disorders

There are numerous disorders of the ovary and female reproductive tract that can be treated with progestrogens, estrogens, and other hormones. These include progestrogen, e.g., progesterone, therapy to inhibit pituitary gonadotropins (precocious puberty in girls), and for prophylaxis to prevent hyperplasia in PCOD. Estrogen therapy is used in the treatment of gonadal failure, control of fertility, and in the management of dysfunctional uterine bleeding. Androgens, gonadotropins, and other hormones are used to treat disorders of the testis, e.g., androgen therapy in hypogonadal men, or gonadotropins to establish or restore fertility in patients with gonadotropin deficiency. Accordingly, these diseases can be treated with implantable devices containing the appropriate hormone-producing cells.

Huntington's Disease

Huntington's disease is characterized by a combination of choreoathetotic movements and progressive dementia usually beginning in midadult life. Distinctive for the disease is atrophy of the caudate nucleus and, to a lesser extent, other structures of the basal ganglia (putamen and globus pallidus). Rodent cells that secrete neurotropic factors have been implanted into the brains of baboons that have a condition similar to Huntington's disease and reversed some of the damaged nerve networks that, in Huntington's patients, lead to progressive loss of control over the body.

Similarly, Huntington's disease in human patients can be treated by the administration of implantable devices that contain human or recombinant cells that secrete the appropriate neurotrophic factors.

Spinal Cord Injuries

The majority of spinal cord injuries result from damage to the surrounding vertebral column, from fracture, dislocation, or both. Treatment of such injuries involves the administration of nerve growth factors such as ciliary neurotropic factor (CNTF), insulin-like growth factor (IGF-1), and neurotropic factors, to enhance the repair of the central and peripheral nervous system. Thus, implantable devices containing cells that secrete such factors, either naturally or through genetic engineering, can be used to treat spinal cord injuries.

Mood (or Affective) Disorders

Mood disorders are a group of mental disorders such as schizophrenia characterized by extreme exaggerations and disturbances of mood and affect associated with physiologic (vegetative), cognitive, and psychomotor dysfunctions. Many mood disorders are associated with medical diseases that can be treated with implantable devices containing the appropriate cells such as hypothyroidism, Parkinson's disease, Alzheimer's disease, and malignancies as discussed herein. In addition, it has been shown that the neurotransmitter 5-hydroxyindol acetic acid (5-HIAA), a serotonin metabolite, is reduced in the cerebral spinal fluid of depressed patients. Deficits in other neurotransmitters such as dopamine and $\gamma$-aminobutyric acid (GABA) have also been identified in patients with major depression. Therefore, implantable devices containing cells that secrete these neurotransmitter are useful to treat these deficiencies.

Motor Neuron Diseases

Degenerative motor neuron diseases include ALS (see above), heritable motor neuron diseases such as spinal muscular atrophy (SMA), and those associated with other degenerative disorders such as olivopontocerebellar atrophies and peroneal muscular atrophy. These diseases can be treated by administration of implantable devices containing cells that secrete neurotropic factors like brain-derived neurotrophic factor (BDNF), and neurotrophin-3 (NT-3).

Acquired Immunodeficiency Syndrome (AIDS)

AIDS is caused by an underlying defect in cell-mediated immunity due to the human immunodeficiency virus (HIV), and causes persistent constitutional symptoms and/or diseases such as secondary infections, neoplasms, and neurologic disease. Patients can be treated to ameliorate symptoms by immunologic augmentation with implantable devices that contain cells genetically engineered to secrete, e.g., recombinant human IL-2 (to decrease suppressor cell activity resulting in an increased T cell adjuvant activity); or recombinant human INF-$\gamma$ (macrophage augmentation). AIDS-related tumors such as Kaposi's sarcoma can be treated with encapsulated cells that secrete human interferon-$\alpha$, interleukin-2 and tumor necrosis factor (TNF).

Amyotrophic Lateral Sclerosis (Lou Gehrig's Disease)

ALS is the most frequently encountered form of progressive motor neuron disease, and is characterized by progressive loss of motor neurons, both in the cerebral cortex and in the anterior horns of the spinal cord, together with their homologs in motor nuclei of the brainstem. ALS can be treated with implantable devices that contain cells that secrete nerve growth factors such as myotrophin, insulin-like growth factor (IGF-1), ciliary neurotropic factor (CNTF), brain-derived neurotrophic factor (BDNF) and neurotrophin-3 (NT-3). Animal studies with these factors (IGF-1 is available from Cephalon, CNTF from Regeneron, and NT-3 from Amgen), have demonstrated that they can stem the degenerative effects caused by nerve damage or disease.

Cancer

In most cases, cancer originates from a single stem cell which proliferates to form a clone of malignant cells. Growth is not properly regulated by the normal biochemical and physical influences in the environment. There is also a lack of normal, coordinated cell differentiation. Cancer cells develop the capacity for discontinuous growth and dissemination to other parts of the body.

Various cancers can be treated according to the invention by the administration of implantable devices containing cells that secrete interferon-α (IFN-α) (for solid tumors, hairy cell leukemia, Kaposi's sarcoma, osteosarcoma, and various lymphomas); recombinant interleukin-2 (IL-2) (for melanoma, renal carcinoma, and Kaposi's sarcoma); tumor necrosis factor (with IL-2 for Kaposi's sarcoma); recombinant human IFN-α and recombinant human colony stimulating factor-granulocyte macrophage (GM-CSF) (for Kaposi's sarcoma); recombinant human INF-γ (for macrophage augmentation); CSF (for aggressive chemotherapy, bone marrow transplantation, priming of leukemic cells to enhance sensitivity to chemotherapy and to support dose intensification); ciliary neurotropic factor (CNTF) and insulin-like growth factor (IGF- 1) (for peripheral neuropathies caused by chemotherapy); adrenal gland cells (for pain relief when injected into the lower spine to secrete natural painkillers) and progesterone-producing cells (for palliation in endometrial and breast carcinoma).

Duchenne's Muscular Dystrophy Duchenne's dystrophy is an X-linked recessive disorder characterized by progressive weakness of girdle muscles, inability to walk after age 12, kyphoscoliosis (curvature of the spine), and respiratory failure after the fourth decide. This disease can be treated by administration of implantable devices containing myoblast cells and growth factors. Myoblasts have been injected into young boys with Duchenne's muscular dystrophy to determine whether the cells can supply a structural protein that is missing. Researchers have observed muscle strength improvement in several of the boys.

Epilepsy

The epilepsies are a group of disorders characterized by chronic, recurrent, paroxysmal changes in neurologic function caused by abnormalities in the electrical activity of the brain. In some forms of focal epilepsy, inhibitory interneurons appear to be preferentially lost. Treatment with neurotropic factors and other neuropeptides such as has been found effective. Therefore, the implantable devices containing cells secreting these factors can be used to treat epilepsy.

It is to be understood that while the invention has been described in conjunction with the detailed description thereof, that the foregoing description is intended to illustrate and not limit the scope of the invention, which is defined by the scope of the appended claims. Other aspects, advantages, and modifications within the scope of the invention will be apparent to those skilled in the art to which the invention pertains.

All patents and publications referred to herein are hereby incorporated by reference.

What is claimed is:

1. An implantable device which includes a living cell or tissue, and an agent that inhibits the ability of a host molecule to damage the living cell or tissue, wherein the agent contacts the living cell or tissue, and the agent and the cell or tissue are disposed within a semi-permeable component.

2. The implantable device of claim 1, wherein the living cell or tissue includes a cell or tissue that is autologous, allogeneic, or xenogeneic with respect to a subject within whom the device is implanted.

3. The implantable device of claim 2, wherein the cell or tissue is from a dog, pig, goat, rabbit horse, cow, sheep, or non-human primate.

4. The implantable device of claim 1, wherein said device is a perfusion device.

5. The implantable device of claim 1, wherein said device is an intravascular device.

6. The implantable device of claim 1, wherein the agent that inhibits the ability of a host molecule to damage the living cell or tissue is an antibody that binds: a host antibody; a component or the host complement system; a host cytokine; or a host inflammatory cytokine.

7. The implantable device of claim 1, wherein the agent inhibits the ability of the host molecule to damage the living cell or tissue by absorbing, adsorbing, binding, degrading, sequestering, or neutralizing the host molecule.

8. The implantable device of claim 1, wherein the agent has a relatively high and specific affinity for a host molecule.

9. The implantable device of claim 1, wherein the agent is a peptide.

10. The implantable device of claim 6, wherein the host antibody is an IgG, IgA, IgM, or IgE antibody.

11. The implantable device of claim 1 wherein said agent comprises an anti-fibrotic agent.

12. A composite microreactor which includes:
   (a) an internal particle comprising:
      (i) a living cell or tissue;
      (ii) an internal gel particle matrix which contains the living cell or tissue;
      (iii) an internal semipermeable particle coating enclosing the internal gel particle matrix; and
   (b) a gel super matrix, in which the internal particle is embedded; and
   (c) an agent that inhibits the ability of a host molecule to damage the living cell or tissue, said agent being disposed in the internal particle.

13. The composite microreactor of claim 12, wherein the agent inhibits the ability of a host molecule to damage the living cell or tissue is an antibody which binds a host antibody.

14. The composite microreactor of claim 12, wherein the agent that inhibits the ability of a host molecule to damage the living cell or tissue is present in said internal particle and additionally in said gel super matrix of the composite microreactor and the concentration of the agent or the number of agent molecules is greater in the gel super matrix.

15. The composite microreactor of claim 12, wherein the internal semipermeable particle coating is a three-part composite layer.

16. The composite microreactor of claim 12, wherein the agent that inhibits the ability of a host molecule to damage the living cell or tissue is an antibody that binds: a host antibody; a component of the host complement system; a host cytokine; or a host inflammatory cytokine.

17. The composite microreactor of claim 12, wherein the living cell or tissue includes a cell or tissue that is autologous, allogeneic, or xenogeneic with respect to a host within which the device is implanted.

18. The composite microreactor of claim 17, wherein the cell or tissue is from a dog, pig, goat, rabbit, horse, cow, sheep, or non-human primate.

19. The composite microreactor of claim 12, wherein the agent inhibits the ability of the host molecule to damage the living cell or tissue by absorbing, adsorbing, binding, degrading, sequestering, or neutralizing the host molecule.

20. The composite microreactor of claim 12, wherein the agent has a relatively high and specific affinity for a host molecule.

21. The composite microreactor of claim 12, wherein the agent is a peptide.

22. The composite microreactor of claim 16, wherein the host antibody is an IgG, IgA, IgM, or IgE antibody.

23. The composite microreactor of claim 12, wherein the agent that inhibits the ability of a host molecule to damage the living cell or tissue is disposed in said internal gel particle matrix.

24. The composite microreactor of claim 12 wherein said agent comprises an anti-fibrotic agent.

25. A double composite microreactor which includes:
  (1) an internal particle comprising:
    (a) a living cell or tissue;
    (b) an internal particle matrix which contains the living cell or tissue;
    (c) an internal particle semipermeable coating enclosing the internal particle matrix; and
  (2) a particle which includes:
    (a) the internal particle of (1),
    (b) a particle matrix in which the internal particle is embedded, and
  (3) a super matrix in which the particle of (2) is embedded; and
  (4) an agent that inhibits the ability of a host molecule to damage the living cell or tissue, said agent being disposed in at least one of the internal particle and the particle.

26. The double composite microreactor of claim 25, wherein the agent that inhibits the ability of a host molecule to damage the living cell or tissue is an antibody which binds host antibodies.

27. The double composite microreactor of claim 25, wherein the agent that inhibits the ability of a host molecule to damage the living cell or tissue is an antibody that binds: a host antibody; a component of the host complement system; a host cytokine; or a host inflammatory cytokine.

28. The double composite microreactor of claim 25, wherein the living cell or tissue includes a cell or tissue that is autologous, allogeneic, or xenogenic to a cell or tissue within a host that is to be treated with the microreactor.

29. The double composite microreactor of claim 28, wherein the cell or tissue is from a dog, pig, goat, rabbit, horse, cow, sheep, or non-human primate.

30. The double composite microreactor of claim 25, wherein the agent that inhibits the ability of a host molecule to damage the living cell or tissue is present in the internal particle and the super matrix, and the concentration or number of the agent in the internal particle is less than the concentration or number of the agent in the supermatrix.

31. The double composite microreactor of claim 25, wherein the agent that inhibits the ability of a host molecule to damage the living cell or tissue is present in the particle and the super matrix, and the concentration or number of the agent in the particle is less than the concentration or number of the agent in the super matrix.

32. The double composite microreactor of claim 25, wherein the internal particle semipermeable coating is a three-part composite layer.

33. The double composite microreactor of claim 25, wherein the internal particle semipermeable coating is not a three-part composite layer but the particle is coated with a three-part composite layer.

34. The double composite microreactor of claim 25, wherein the agent that inhibits the ability of a host molecule to damage the living cell or tissue is additionally present in said super matrix of the composite microreactor.

35. The double composite microreactor of claim 25, wherein the agent that inhibits the ability of a host molecule to damage the living cell or tissue is present in the internal particle and the particle, and the concentration of the agent or the number of agent molecules in the internal particle is less than the concentration of the agent or the number of agent molecules in the particle.

36. The double composite microreactor of claim 25, wherein the agent inhibits the ability of the host molecule to damage the living cell or tissue by absorbing, adsorbing, binding, degrading, sequestering, or neutralizing the host molecule.

37. The double composite microreactor of claim 25, wherein the agent has a relatively high and specific affinity for a host molecule.

38. The double composite microreactor of claim 25, wherein the agent is a peptide.

39. The double composite microreactor of claim 26, wherein the host antibody is an IgG, IgA, IgM, or IgE antibody.

40. The double composite microreactor of claim 25 wherein said agent comprises an anti-fibrotic agent.

41. The double composite microreactor of claim 25, wherein the agent that inhibits the ability of a host molecule to damage the living cell or tissue is disposed in the particle matrix.

42. The double composite microreactor of claim 25, wherein the agent that inhibits the ability of a host molecule to damage the living cell or tissue is disposed in the internal particle matrix.

43. The double composite microreactor of claim 25, wherein the agent is disposed in the internal particle and the particle.

44. The double composite microreactor of claim 25, wherein the agent is disposed in the internal particle and the super matrix.

45. The double composite microreactor of claim 25, wherein the agent is disposed in the particle and the super matrix.

46. A composite microreactor comprising:
  (1) an internal particle comprising:
    (a) a living cell or tissue;
    (b) an internal gel particle matrix that contains the living cell or tissue; and
    (c) an internal semipermeable particle coating enclosing the internal gel particle matrix;
  (2) a gel super matrix in which the internal particle is embedded; and
  (3) an antibody that binds a host antibody; a component of the host complement system; a host cytokine; or a host inflammatory cytokine, disposed in the internal particle.

47. A double composite microreactor comprising:
  (1) an internal particle which includes:
    (a) a living cell or tissue;
    (b) an internal particle matrix which contacts the living cell or tissue; and
    (c) an internal particle semipermeable coating enclosing the internal particle matrix; and
  (2) a particle which includes:
    (a) the internal particle (1),
    (b) a particle matrix in which the internal particle is embedded;

(3) a super matrix, in which the particle of (2) is embedded; and
(4) an antibody that binds a host antibody; a component of the host complement system; a host cytokine; or a host inflammatory cytokine, disposed in at least one of the internal particle and the particle.

* * * * *